United States Patent
Prockop et al.

(10) Patent No.: US 6,974,571 B2
(45) Date of Patent: Dec. 13, 2005

(54) ISOLATED STROMAL CELLS AND METHODS OF USING THE SAME

(75) Inventors: Darwin J. Prockop, Philadelphia, PA (US); Ruth F. Pereira, Lansdowne, PA (US); Dennis B. Leeper, Wynnewood, PA (US); Michael D. O'Hara, Wyncote, PA (US); Joseph Kulkosky, Philadelphia, PA (US); Donald Phinney, Maple Glen, PA (US); Alexey Laptev, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 08/913,918

(22) PCT Filed: Mar. 28, 1996

(86) PCT No.: PCT/US96/04407

§ 371 (c)(1),
(2), (4) Date: Dec. 8, 1997

(87) PCT Pub. No.: WO96/30031

PCT Pub. Date: Oct. 3, 1996

(65) Prior Publication Data

US 2003/0059412 A1 Mar. 27, 2003

Related U.S. Application Data

(63) Continuation-in-part of application No. 08/412,066, filed on Mar. 28, 1995, now Pat. No. 5,716,616
(60) Provisional application No. 60/006,627, filed on Nov. 13, 1995.

(51) Int. Cl.[7] .......................... A61K 48/00; C12N 15/00
(52) U.S. Cl. ................................ 424/93.21; 435/320.1; 435/69.1; 435/91.4
(58) Field of Search ................................ 424/93.21, 423, 424/425; 435/320.1, 69.1, 455, 325, 91.4

(56) References Cited

U.S. PATENT DOCUMENTS 4,391,909 A    7/1983   Lim (Continued)

FOREIGN PATENT DOCUMENTS

| EP | 0 381 490 A | 8/1990 |
| WO | WO 95/05835 | 3/1995 |

OTHER PUBLICATIONS

Lennon, Experimental Cell Res., vol. 219, 211–222, 1995.*

(Continued)

*Primary Examiner*—Dave Trong Nguyen
(74) *Attorney, Agent, or Firm*—Drinker Biddle & Reath LLP

(57) ABSTRACT

Methods of treating patients who are suffering from a disease, disorder or condition characterized by a bone cartilage or lung defect are disclosed. The methods comprising the step of intravenous administration of stromal cells isolated from normal syngeneic individuals or intravenous administration of stromal cells isolated from the patient subsequent to correction of the genetic defect in the isolated cells. Implant devices comprising a container that has at least one membrane surface and stromal cells isolated from bone marrow that comprise a gene construct are disclosed. The gene construct in the stromal cells comprises a nucleotide sequence that encodes a beneficial protein operably linked to regulatory elements which function in stromal cells. Methods of treating individuals with diseases, disorders or conditions which can be treated with a beneficial protein, including diseases, disorders or conditions characterized by gene defects are disclosed. The methods comprise introducing into such individuals, stromal cells that are administered in a manner that physically isolates them from the recipient's immune system and that comprise a gene construct that comprises a nucleotide sequence that encodes a beneficial protein operably linked to regulatory elements which function in stromal cells.

16 Claims, 2 Drawing Sheets

U.S. PATENT DOCUMENTS

| | | | |
|---|---|---|---|
| 4,806,355 A | | 2/1989 | Goosen et al. |
| 4,902,295 A | | 2/1990 | Walthall et al. |
| 4,904,259 A | | 2/1990 | Itay .............................. 623/16 |
| 4,942,129 A | | 7/1990 | Goosen et al. |
| 4,997,443 A | | 3/1991 | Walthall et al. |
| 5,082,670 A | | 1/1992 | Gage et al. ................. 424/520 |
| 5,197,985 A | * | 3/1993 | Caplan et al. ................ 623/16 |
| 5,314,471 A | | 5/1994 | Brauker et al. |
| 5,334,640 A | | 8/1994 | Desai et al. |
| 5,344,454 A | | 9/1994 | Clarke et al. |
| 5,591,625 A | | 1/1997 | Gerson et al. |
| 5,670,351 A | * | 9/1997 | Emerson et al. |
| 5,830,708 A | * | 11/1998 | Naughton .................. 435/70.1 |
| 5,843,431 A | * | 12/1998 | Schinstine et al. ........ 424/93.21 |
| 5,846,796 A | * | 12/1998 | Cerami et al. |
| 5,858,721 A | * | 1/1999 | Naughton et al. .......... 435/69.1 |
| 5,876,452 A | * | 3/1999 | Athannasiou et al. ......... 623/16 |
| 5,899,936 A | * | 5/1999 | Goldstein ................... 128/898 |
| 5,942,225 A | * | 8/1999 | Bruder et al. .............. 424/93.7 |
| 5,962,323 A | * | 10/1999 | Greenberger et al. |
| 6,013,853 A | * | 1/2000 | Athannasiou et al. ......... 623/11 |
| 6,087,113 A | * | 7/2000 | Caplan et al. ............... 435/7.1 |

OTHER PUBLICATIONS

Considine, J. Clin. Invest. vol. 95, pp. 2986–2988, 1995.*
Naughton, Somatic Cell and Molecular Genetics, vol. 18, No. 5, pp. 451–462, 1992.*
Gilbert, Transplantation, vol. 56, pp. 423–427, 1993.*
Report and recommendations of the panel to assess the NIH investment in research on gene therapy Orkin et al. Dec. 7, 1995.*
Hoogerbrugge et al., Bone marrow gene transfer in three patients with adenosine deaminase deficiency, 1996, Gene Thereapy, vol. 3, pp. 179–183.*
Hoeben et al., Toward Gene Therapy for Hemophilla A: Long–Term Persistence of Factor V–III–Secreting . . . , 1993, Human Gene Therapy, vol. 4, pp. 179–186.*
Kohn, The current status of gene therapy using hematopoietic stem cells, 1995, Current Opinion in Pediatrics, vol. 7, pp. 56–63.*
Onodera et al., Gene Therapy of Severe Combined Immunodeficiecy Caused by Adenosine . . . , 1999, Acta Haematol, vol. 101, pp. 89–96.*
Moritz et al., Bone Marrow Extracelluar Matrix Molecules Improve Gene Transfer into Human Hematopietic Cells via Retroviral Vector, Apr. 1994, J. Clin. Invest., vol. 93, pp. 1451–1457.*
Gronthos et al., The Biology and Application of Human Bone Marrow Stromal Cell Precursors, 1996, Journal of Hematotherapy, vol. 5, pp. 1996.*
Riddell et al., T–Cell mediated rejection of gene–modified HIV–specific cytotoxic T lymphocytes in HIV–infected patients, Feb. 1996, Nature Medicine, vol. 2, No. 2, pp. 216–220.*
Anderson, Human gene therapy, Apr. 30, 1998, Nature, pp. 25–30.*
Verma et al., Gene therapy–promises, problems and propects, Sep. 18, 1997, Nature, vol. 389, pp. 239–242.*
Marshall, Gene Therapy's Growing Pains, Aug. 25, 1995, vol. 269, pp. 1050–1055.*
Coccia et al., N. Eng. J. Med., 1980, 302(13):702–707.
R.F. Pereira et al., Proc. Natl. Acad. Sci. USA, 1995, 92:4857–4861.
Castro–Malaspina H. et al., Blood, 1980, 56(2):289–301.
Prockop, 1997, Science 276:71–74.
El–Badri–Dajani et al., 1996, Cell Transplantation 5:5S2:36.
Denizot et al., 1998, Biochimica et Biophysica 1402:209–215.
Huss et al., 1995, Cell Transplantation, 4:483–491.
Kadiyala et al., 1997, Cell Transplantation 6:125–134.
Sykes and Sachs, 1990, Immunology 2:401–417.
Rosenberg et al., 1988, Science 242:1575–1578.
Gage et al., 1991, Trends in Neurosciences 14:328–333.
Freed et al., 1990, Progress in Brain Research 82:11–21.
Wolff et al., 1989, Proc. Natl. Acad. Sci., 86:9011–9014.
Gage et al., 1987, Neuroscience 23:795–807.
Sloan et al., 1991, Trends in Neurosciences 14:341–346.
Ala–Kokko et al., 1991, J. Biol. Chem. 266:14175–14178.
Andersson et al., 1993, Int. J. Dev. Neurosci.11:555–568.
Andreason et al., 1988, Bio Techniques 6:650–660.
Anklesaria, 1987, PNAS USA 84:7681–7685.
Applebaum et al., 1992, Blood 80(6):1608–1613.
Arner, P., 1995, N. England J. Med. 333–382.
Benayahu et al., 1989, J. Cell Physiol. 140:1–7.
Bennett et al., 1991, J. Cell. Sci. 99:131–139.
Beresford et al., 1992, J. Cell. Sci.102:341–351.
Bienzle et al., 1994, Proc. Natl. Acad. Sci USA, 91:350–354.
Bjorklund, 1993, Nature 362:414–415.
Bradham et al., 1994, J. Cell Physiol.158:61–68.
Caplan, 1991, J. Orthop. Res. 9:641–650.
Carter et al., 1992, Blood 79:356–364.
Castro–Malaspina et al., 1980, Blood 56:289–301.
Coccia, P.F. et al, 1980, New England Journal of Medicine, 302,13:702–707.
Considine et al., 1995, J. Clin. Invest. 95:2986–2988.
Emorine, L. et al., 1994, Trends Pharmacol. Sci., 15,3.
Flier, J.S., 1995, Cell, 80:15.
Freed et al., 1992, N. Engl. J. Med 327:1549–1555.
Friedenstein et al., 1987, Cell Tissue Kinet. 20:263–272.
Friedenstein et al., 1976, Exp. Hemat. 4:267–274.
Kang et al., 1993, J. Neurosci. 13:5203–5211.
Khillan et al., 1991, J. Biol. Chem. 266:23373–23379.
Kiefer, 1991, Blood 78(10):2577–2582.
Liesveld et al., 1989, Blood 73:1794–1800.
Liesveld et al., 1990, Exp. Hematot. 19:63–70.
Lowell, B.B. et al., 1995, J. Clin. Invest., 95:923.
Mardon et al., 1987, Cell Tissue Res. 250:157–165.
Mercer et al., 1992, In: Antisense Strategies, Ann. IV. Y. Acad. Sci. Biol. 660:209–218.
Miller, A.D. and Rosman, G.J. 1989 BioTechniques 7:980–990.
Morrison et al, 1994, Nature 367:284–287.
Nakagawa, T., et al., 1993, Arthritis and Rheumatism, 36,2:263–268.
Nakahara et al., 1991, J. Orthop. Res. 9:465–476.
Niedzwiedski et al., 1993, Biomaterials 14:115–121.
O'Hara et al., 1991, Exp. Hemat. 19:878–881.
Ohgushi et al., 1989, Acte. Orthop. Scand. 60:334–339.
Owen et al., 1988, in Cell and Molecular Biology of Vertebrate Hard Tissues, Ciba Foundation Symposium 136, Chichester, UK, pp. 42–60.
Pereira et al., 1995, Proc. Natl. Acad. Sci. USA 92:4857–4861.
Pereira et al., 1983, J. Clin. Invest. 91:709–716.
Piersma et al. 1983, Brit. J. Hematol. 94:285–290.
Piersma et al., 1985, Exp. Hematol 13:237–243.
Rink, T.J. et al., 1994, Nature, 372–406.
Rosenstein, 1995, Exp. Neurol. 133:1–6.
Simmons et al., 1991, Blood 78:55–62.

Smith et al., 1993, Mature Genet. 5:397–402.
Sokolov et al., 1995, J. Biol. Chem. 270:9622–9629.
Sokolov et al., 1993, Biochemistry 32:9242–9249.
Spencer et al., 1992, N. Engl. J. Med. 327:1541–1548.
Stewart et al. 1993, Blood 81:2566–2571.
Toneguzzo et al., 1986, Mol. Call. Biol. 6:703–706.
Turner et al., 1993, Neurosurg. 33:1031–1037.
Wakitani et al., 1994, J. Bone & Surg. 76A:579–592.
Zhou et al., 1992, J. Comp. Neurol. 317:145–155.

* cited by examiner

ISOLATED STROMAL CELLS AND METHODS OF USING THE SAME

CROSS REFERENCE TO RELATED APPLICATIONS

The present application is a national stage application filed under 35 U.S.C. § 371, claiming the benefit of priority of International Application No. PCT/US96/04407, filed Mar. 28, 1996, which is a continuation-in-part of U.S. application Ser. No. 08/412,066, filed Mar. 28, 1995 (issued on Feb. 10, 1998 as U.S. Pat. No. 5,716,616), and which claims the benefit under 35 U.S.C. § 119(e) of U.S. Provisional Application No. 60/006,627, filed on Nov. 13, 1995, all of which are herein incorporated by reference in their entirety.

FIELD OF THE INVENTION

The present invention relates to compositions comprising isolated stromal cells, to containers which comprise isolated stromal cells transfected with exogenous DNA, to methods of treating individuals suffering from diseases associated with bone and cartilage, and to methods of using stromal cells in the treatment of individuals who have diseases associated with bone, cartilage or lung tissue, diseases associated with dermis, blood vessels, heart and kidney tissue, diseases associated with genetic defects and/or diseases or conditions that can be treated by administering or delivering beneficial proteins.

BACKGROUND OF THE INVENTION

In addition to hematopoietic stem cells, bone marrow contains "stromal cells" which are mesenchymal precursor cells (Friedenstein, A. J. et al., *Exp. Hemat.* 4:267–274 (1976) which is incorporated herein by reference) that are characterized by their adherence properties when bone marrow cells are removed and put on to plastic dishes. Within about four hours, stromal cells adhere to the plastic and can thus be isolated by removing non-adhered cells form the dishes. These bone marrow cells that tightly adhere to plastic have been studied extensively (Castro-Malaspina, H. et al., *Blood* 56:289–301 (1980); Piersma, A. H. et al., *Exp. Hematol* 13:237–243 (1985); Simmons, P. J. and Torok-Storb, B., *Blood* 78:55–62 (1991); Beresford, J. N. et al., *J. Cell. Sci.* 102:341–351 (1992); Liesveld, J. L. et al., *Blood* 73:1794–1800 (1989); Liesveld, J. L. et al., *Exp. Hematot* 19:63–70 (1990); and Bennett, J. H. et al., *J. Call. Sci.* 99:131–139 (1991)) which are incorporated herein by reference. As used herein, the term "adherent cells" is meant to refer to stromal cells and the term "non-adherent cells" is meant to refer to hematopoietic precursor cells.

Stromal cells are believed to participate in the creation of the microenvironment with the bone marrow in vivo. When isolated, stromal cells are initially quiescent but eventually begin dividing so that they can be cultured in vitro. Expanded numbers of stromal cells can be established and maintained. Stromal cells have been used to generate colonies of fibroblastic adipocytic and osteogenic cells when cultured under appropriate conditions. If the adherent cells are cultured in the presence of hydrocortisone or other selective conditions populations enriched for hematopoietic precursors or osteogenic cells are obtained (Carter, R. F. et al., *Blood* 79:356–364 (1992) and Bienzle, D. et al., *Proc. Natl. Acad. Sci USA,* 91:350–354 (1994)) which are incorporated herein by reference.

There are several examples of the use of stromal cells. European Patent EP 0,381,490, which is incorporated herein by reference, discloses gene therapy using stromal cells. In particular, a method of treating hemophilia is disclosed. Stromal cells have been used to produce fibrous tissue, bone or cartilage when implanted into selective tissues in vivo (Ohgushi, H. et al., *Acte. Orthop. Scand.* 60:334–339 (1989); Nakahara, H. et al. *J. Orthop. Res.* 9:465–476 (1991); Niedzwiedski, T. et al., *Biomaterials* 14:115–121 (1993); and Wakitani, S. et al., *J. Bone & Surg.* 76A:579–592 (1994)). In some reports, stromal cells were used to generate bone or cartilage in vivo when implanted subcutaneously with a porous ceramic (Ohgushi, H. et al. Acta. Orthop. Scand. 60:334–339 (1989)), intraperitoneally in a diffusion chamber (Nakahara, H. et al. J. Orthop. Res. 9:465–476 (1991)), percutaneously into a surgically induced bone defect (Niedzwiedski, T. et al. Biomaterials. 14:115–121 (1993)), or transplanted within a collagen gel to repair a surgical defect in a joint cartilage (Wakitani, S. et al. J. Bone & Surg. 76A:579–592(1994)). Piersma, A. H. et al. *Brit. J. Hematol.* 54:285–290 (1983) disclose that after intravenous bone marrow transplantation, the fibroblast colony-forming cells which make up the hemopoietic stroma lodge and remain in the host bone marrow. Stewart et al. (*Blood* 81:2566–2571 (1993)) recently observed that unusually large and repeated administrations of whole marrow cells produced long-term engraftment of hematopoietic precursors into mice that had not undergone marrow ablation. Also, Bienzle et al. (*Proc. Natl. Acad. Sci USA,* 91:350–354 (1994)) successfully used long-term bone marrow cultures as donor cells to permanently populate hematopoietic cells in dogs without marrow ablation. In some reports, stromal cells were used either as cells that established a microenvironment for the culture of hematopoietic precursors (Anklesaria, *PNAS USA* 84:7681–7685 (1987)) or as a source of an enriched population of hematopoietic stem cells (Kiefer, *Blood* 78(10):2577–2582 (1991)).

SUMMARY OF THE INVENTION

One aspect of the present invention relates to methods of treating patients who are suffering from a disease, disorder or condition characterized by a bone, cartilage or lung defect or diseases disorder or condition characterized by defects in dermis, blood vessels, heart or kidney. The method comprises the steps of: obtaining a bone marrow sample from a normal, matched, syngeneic donor; isolating adherent cells from the sample; and administering the isolated adherent cells to the patient by intravenous infusion. Another aspect of the present invention relates to methods of treating patients who are suffering from a disease, disorder or condition that characterized by a mutated, non-functioning or under-expressed gene which results in a defect in the patient's bones, cartilage or lungs or dermis, blood vessels, heart or kidney. The method comprises the steps of obtaining a bone marrow sample from the patient or a matched syngeneic donor, isolating adherent cells from the sample, transfecting said adherent cells with a normal copy of said mutated, non-functioning or under-expressed gene that is operably linked to functional regulatory elements, and administering the transfected adherent cells to the patient intravenously.

The present invention relates to implant devices that comprise a container having at least one membrane surface and stromal cells. The stromal cells comprise a gene construct, which includes a nucleotide sequence that encodes a beneficial protein operably linked to regulatory elements which function in stromal cells.

The invention relates to methods of treating individuals who have diseases, disorders or conditions which can be treated with a beneficial protein, including diseases, disorders or conditions characterized by genetic defects. The methods comprise the step of introducing into such individuals, immunologically isolated stromal cells that comprise a gene construct. The gene construct comprises a nucleotide sequence that encodes a beneficial protein operably linked to regulatory elements which function in stromal cells.

The invention relates to stromal cells that comprise a gene construct and that are administered in a manner that physically isolates them from the host's immune system. The gene construct comprises a nucleotide sequence that encodes a beneficial protein operably linked to regulatory elements which function in stromal cells.

DETAILED DESCRIPTION OF THE INVENTION

Figure 1:
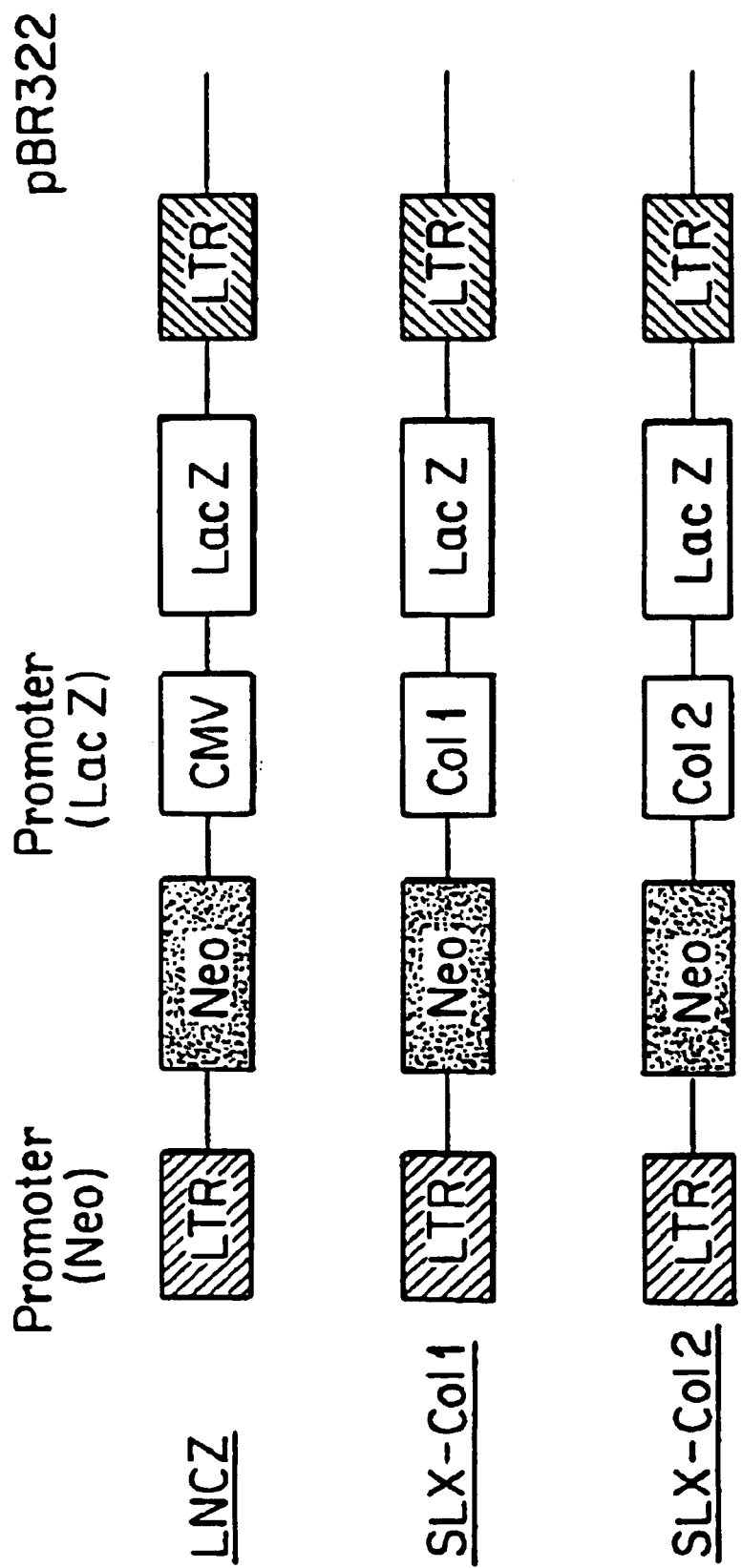
FIG. 1 shows a schematic of the retroviral constructs pCMV-lac Z, pCOL1-lac Z, and pCOL2-lac Z. The cassettes of the gene constructs are: LTR-Neo-promoter-Lac Z-LTR.

As used herein, "stromal cells", "colony forming fibroblasts", "marrow stromal cells", "adherent cells" and "MSCs" are used interchangeably and meant to refer to the small fraction of cells in bone marrow which can serve as stem-cell-like precursors of osteocytes, chondrocytes, and adipocytes and which can be isolated from bone marrow by their ability adhere to plastic dishes. Stromal cells may be derived form any animal. In some embodiments, stromal cells are derived from primates, preferably humans.

As used herein, "diseases, disorders and conditions characterized by a gene defect" is meant to refer to diseases, disorders and conditions in which defective genes and/or insufficient gene expression is causally linked to the disease or symptoms. Individual who have any of several well known diseases, disorders and conditions characterized by a gene defect can be identified by those having ordinary skill in the art. Examples of diseases, disorders and conditions characterized by a gene defect include, but are not limited to, growth hormone deficiency, diabetes, adenine deaminase deficiency, hemophilia A and hemophilia B. The methods and means for diagnosing each such condition is well known.

As used herein, the term "disease, disorder or condition characterized by a bone, cartilage or lung defect" is meant to refer to diseases, disorders and conditions which are caused by a genetic mutation in a gene that is expressed by bone cells, cells which make cartilage or lung cells such that one of the effects of such a mutation is manifested by abnormal structure and/or function of the bone, cartilage and lungs respectively.

As used herein, the term "disease, disorder or condition characterized by a defect in the dermis, blood vessels, heart and kidney" is meant to refer to diseases, disorders and conditions which are caused by a genetic mutation in a gene that is expressed by cells of the dermis, blood vessels, heart and kidney such that one of the effects of such a mutation is manifested by abnormal structure and/or function of the dermis, blood vessels, heart and kidney respectively. Examples of diseases, disorders and conditions characterized by a defect in the dermis includes burns, bed sores and diabetic ulcers.

As used herein, "diseases, disorders and conditions characterized by a gene defect of a gene which encodes a secreted protein" is meant to refer to diseases, disorders and conditions characterized by a gene defect in which the gene that is defective genes or insufficiently expressed encodes a protein that is normally secreted.

As used herein, "diseases, disorders and conditions which can be treated with beneficial proteins" is meant to refer to diseases, disorders and conditions that can be treated or prevented by the presence of a protein which alleviates, reduces, prevents or causes to be alleviated, reduced or prevented, the causes and/or symptoms that characterize the disease, disorder or condition. Diseases, disorders and conditions which can be treated by with proteins includes diseases, disorders and conditions characterized by a gene defect as well as those which are not characterized by a gene defect but which nonetheless can be treated or prevented by the presence of a protein which alleviates, reduces, prevents or causes to be alleviated, reduced or prevented, the causes and/or symptoms that characterize the disease, disorder or condition.

As used herein, "immunologically isolated", "immunologically protected", "immunologically neutralized", and "a manner that physically isolates them from the recipient's immune system" are meant to refer to the encapsulation, containment or other physical separation of an implanted cell from the body into which it is implanted such that the cell is not exposed to and cannot be eliminated by the immune system of the body such that cells which are immunologically isolated are administered in a manner that physically isolates them from the recipient's immune system. Examples of immunological isolation means include, but are not limited by, well known technologies and devices such as microencapsulation, biocompatible matrices, diffusion chambers, implantable cartridges, implant devices with membrane assemblies and other containers with membranes. It is preferred that cells are immunologically isolated by maintaining them with implant devices.

As used herein, "beneficial protein" and "heterologous protein" are interchangeable and are meant to refer to 1) proteins which can compensate for the protein encoded by defective genes and/or insufficient gene expression that is causally linked to the disease or symptoms in diseases, disorders and conditions characterized by a gene defect and 2) proteins whose presence alleviates, reduces, prevents or causes to be alleviated, reduced or prevented, the causes and/or symptoms that characterize diseases, disorders and conditions which can be treated with beneficial proteins.

As used herein, "gene construct" is meant to refer to foreign recombinant nucleic acid molecules which include coding sequences that encode beneficial proteins operably linked to regulatory elements sufficient for expression of the coding sequence in stromal cells.

As used herein, "foreign recombinant nucleic acid molecules" is meant to refer to recombinant nucleic acid molecules which either are not present in stromal cells or are not expressed as proteins in sufficiently high levels in stromal cells until they are introduced into the cell by means such as but not limited to classical transfection ($CaPO_4$ or DEAE dextran), electroporation, microinjection, liposome-mediated transfer, chemical-mediated transfer, ligand mediated transfer or recombinant viral vector transfer.

As used herein, "heterologous gene" is meant to refer to the coding sequence of the gene construct.

As used herein, the terms "exogenous genetic material" and "exogenous gene" are used interchangeably and meant to refer to genomic DNA, cDNA, synthetic DNA and RNA, mRNA and antisense DNA and RNA which is introduced into the stromal cell. The exogenous genetic material may be heterologous or an additional copy or copies of genetic material normally found in the individual or animal. When cells are used as a component of a pharmaceutical composition in a method for treating human diseases, conditions or disorders, the exogenous genetic material that is used to transform the cells may encode proteins selected as therapeutics used to treat the individual and/or to make the cells more amenable to transplantation.

As used herein, "transfected stromal cells" is meant to refer to stromal cells to which a gene construct has been provided through any technology used to introduce foreign nucleic acid molecules into cells such as, but not limited to, classical transfection ($CaPO_4$ or DEAE dextran), electroporation, microinjection, liposome-mediated transfer, chemical-mediated transfer, ligand mediated transfer or recombinant viral vector transfer.

Some aspects of the present invention arise from the discovery that some stromal cells which are introduced into a patient develop into bone, cartilage and lung while others remain precursors cells which throw off daughter cells that develop into bone, cartilage and lung. This discovery allows for the successful treatment of individuals suffering from diseases, conditions and disorders associated with defects in bone, cartilage or lung cells by either providing such individuals with stromal cells from a normal, matched syngeneic donor or by isolating stromal cells from the patient, culturing them and genetically modifying them to correct whatever genetic defect is responsible for the diseases, conditions and disorders associated with defects in bone, cartilage or lung cells. Similarly, it is believed that stromal cells will also develop into cells of the dermis, blood vessels, heart and kidneys, or throw off daughter cells that will do so.

The discovery that isolated, cultured stromal cells repopulate tissue, particularly bone, cartilage and lung tissue, when administered into the bloodstream of an individual makes them suited for treating individuals suffering from diseases, conditions and disorders associated with defects in bone, cartilage or lung cells. The discovery that some isolated, cultured stromal cells, when administered into the blood stream of an individual, act as precursor cells which produce daughter cells that then mature into differentiated cells makes the invention particularly useful because it allows for the long term and continued presence of donated normal or genetically modified cells without the need for continuous readministration of cells. Similarly, the development of stromal cells into cells of the dermis, blood vessels, heart and kidneys, or throw off daughter cells allows for the treatment of diseases effecting those tissues by similar means.

Accordingly, stromal cells from a matched donor may be administered intravenously to individuals suffering from diseases involving bone, cartilage or lung cells, or dermis, blood vessel, heart or kidney cells, in order to augment or replace the individual's bone, cartilage or lung cells, or dermis, blood vessel, heart or kidney cells. Stromal cells from a matched donor may be administered intravenously to individuals suffering from diseases associated with defective gene expression in bone, cartilage or lung cells, or dermis, blood vessel, heart or kidney cells, in order to replace the individuals bone, cartilage or lung cells, or dermis, blood vessel, heart or kidney cells, that don't express or under express a normal gene and/or express a mutated scene. Stromal cells may also be transfected with heterologous genes in gene therapy protocols. According to such aspects of the invention, matched donor stromal cells or stromal cells from an individual may be removed and genetically altered prior to reintroducing the cells into the individual. The cells may be genetically altered to introduce a gene whose expression has therapeutic effect on the individual. According to some aspects of the invention, stromal cells from an individual may be genetically altered to replace a defective gene and/or to introduce a gene whose expression has therapeutic effect on the individual.

In some aspects of the invention, individuals suffering from diseases and disorders that affect bone and that are characterized by a genetic defect may be treated by supplementing, augmenting and/or replacing defective or deficient bone cells with cells that correctly express a normal gene. The cells may be derived from stromal cells of a normal matched donor or stromal cells from the individual to be treated. If derived from the individual to be treated, the cells may be genetically modified to correct the defect. An example of a disease or disorder that affects bone and that is characterized by a genetic defect is osteogenesis imperfecta. Another example of a disease or disorder that affects bone and that is characterized by a genetic defect is osteoporosis. Osteoporosis is frequently regarded as a multifactorial disease to which environmental factors such as diet and exercise contribute. However, studies of disease in twins, large families and large populations demonstrate that many individuals develop the disease primarily because of a genetic defect (see Morrison et al. *Nature* 367:284–287 (1994)). Individuals suffering from osteogenesis imperfecta may be administered stromal cells from a normal matched donor which replace the bone cells in the individual which have a mutated collagen gene. In such embodiments, the normal cells will compensate for the defective cells. In some embodiments, the normal cells may be prepared from the individual's own stromal cells, since cells with a mutated collagenous defect have a growth disadvantage compared to normal cells when grown in culture. Therefore, if stromal cells from an individual with osteogenesis imperfecta are grown as culture, they will gradually become enriched for normal cells. This embodiment will be particularly effective if the individual is a mosaic for the mutated collagen so that some of his or her cells contained the mutated collagen gene and others do not. In an alternative embodiment, stromal cells are isolated from an individual suffering from osteogenesis imperfecta and a normal gene for collagen I is inserted into the isolated stromal cells. The transfected cells are then reintroduced into the individual. A few individuals suffering from osteoporosis also have mutations in one of the two genes for collagen I and the same embodiments, will compensate for the defective cells. In most individuals with osteoporosis, the genes at fault are still unknown but are likely to be identified soon. In such individuals, normal cells will compensate for the defect. Also, when the genes at fault are identified and isolated, an alternative embodiment will be to isolate stromal cells from the individual, insert normal copy or copies of the mutated gene, and reintroduce the cells to the individual.

In some aspects of the invention, individuals suffering from diseases and disorders that affect cartilage and that are characterized by a genetic defect can be treated by supplementing, augmenting and/or replacing defective cells with cells that correctly express a normal gene. The cells may be derived from stromal cells of a normal matched donor or stromal cells from the individual to be treated. If derived from the individual to be treated, the cells may be genetically modified to correct the defect. An example of a disease or disorder that affects cartilage and that is characterized by a genetic defect is chondrodysplasia which cause severe dwarfism, severe problems with joints and related problems. Individuals suffering from chondrodysplasia may be administered stromal cells from a normal matched donor which replace the cells that produce cartilage in the individual which have a mutated collagen gene. In such embodiments, the normal cells will compensate for the defective cells. In an alternative embodiment, stromal cells are isolated from an individual suffering from chondrodysplasia and a normal gene for collagen II is inserted into the isolated stromal cells. The transfected cells are then reintroduced into the individual. The embodiment with the collagen II gene will be useful for the 20% to 90% of individuals with various types of severe chondrodysplasia. The remaining individuals with chondrodysplasia have mutations in other collagen genes (collagen X and X1), in other genes (fibroblast growth factor receptor 3), and in still unidentified genes. In such individuals, normal cells will compensate for the defective cells. Also, an alternative embodiment will be to isolate stromal cells from the individual, insert a normal copy or copies of the mutated gene, and reintroduce the cells to the individual. Another example of a disease or disorder that affects cartilage is osteoarthritis. Osteoarthritis is a heterogeneous disease both in terms of etiology and manifestations. Some individuals develop the degeneration of cartilage in joints that characterize osteoarthritis because of trauma or the late sequelae of infections. A few individuals develop osteoarthritis in multiple joints because of mutations in the gene for collagen II similar to the mutations in the gene that cause chondrodysplasia. Such individuals may or may not show signs of a mild chondrodysplasia. The cause of osteoarthritis in other individuals is unknown, but studies in large families suggest that the disease is inherited and therefore caused mutations is still unidentified genes. Therefore the same embodiments that will be useful to compensate for mutated genes in individuals with chondrodysplasia will also be useful for many individuals with osteoarthritis.

In some aspects of the invention, individuals suffering from diseases and disorders that affect the lungs and that are characterized by a genetic defect can be treated by supplementing, augmenting and/or replacing defective cells with cells that correctly express a normal gene. The cells may be derived from stromal cells of a normal matched donor or stromal cells from the individual to be treated. If derived from the individual to be treated, the cells may be genetically modified to correct the defect. An example of a disease or disorder that affects the lungs and that is characterized by a genetic defect is cystic fibrosis. Another example of a disease or disorder that affects the lungs and that is characterized by a genetic defect is a deficiency of α1-antitrypsin. Individuals suffering from cystic fibrosis may be administered stromal cells from a normal matched donor which have a norma cystic fibrosis to replace or supplement the lungs cells in the individual which have a mutated cystic fibrosis gene. In such embodiments, the normal cells will compensate for the defective cells. In an alternative embodiment, stromal cells are isolated from an individual suffering from cystic fibrosis and a normal cystic fibrosis gene is inserted into the isolated stromal cells. The transfected cells are then reintroduced into the individual.

In some aspects, individuals suffering from diseases of the bone, cartilage and lungs as well as those suffering from diseases of the dermis, blood vessels, heart and kidneys can be treated by isolated stromal cells, expanding their number and systemically adminstering the expanded, rejuvinated stromal cells. Some of the rejuvinated stromal cells will develop into normal bone, cartilage, lung, dermis, blood vessel, heart or kidney cells. Normal stromal cells expand more quickly the defective ones and the expanded rejuvinated populatation will reflect a greater proportion of normal cells. Table 1 describes media useful to culture expanded rejuvinated cultures of isolated stromal cells.

In addition to replacing cells that are defective with repaired cells or normal cells from matched donors, the invention may also be used to express desired proteins that are secreted. That is, stromal cells may be isolated, furnished with a gene for a desired protein and introduced into an individual within whom the desired protein would be produced and exert or otherwise yield a therapeutic effect. This aspect of the invention relates to gene therapy in which therapeutic proteins are administered to an individual.

According to some aspects of the present invention, immunologically isolated transfected stromal cells are used as cell therapeutics to treat diseases, disorders and conditions characterized by a gene defect and/or diseases, disorders and conditions which can be treated with proteins. In particular, gene constructs that comprise heterologous genes which encode beneficial proteins are introduced into stromal cells. The transfected stromal cells are then immunologically isolated and implanted into an individual who will benefit when the protein is expressed and secreted by the cell into the body.

Immunologically isolated stromal cells are particularly useful in cell therapeutic compositions, because in addition to being suitable hosts for expressing heterologous genes and producing heterologous proteins, stromal cells perform favorably when they are immunologically isolated. Immunologically isolated stromal cells have a very high viability when implanted in locations that lack a direct vascular blood supply. Moreover, stromal cells can be easily and readily obtained, they rapidly expand in culture making them a good source of an adequate supply of useful cells for immunologically isolated cell therapeutics.

According to the present invention, gene constructs which comprise nucleotide sequences that encode heterologous proteins are introduced into stromal cells. That is, the cells are genetically altered to introduce a gene whose expression has therapeutic effect on the individual. According to some aspects of the invention, stromal cells from an individual or from another individual or from a non-human animal may be genetically altered to replace a defective gene and/or to introduce a gene whose expression has therapeutic effect on the individual.

According to the present invention, stromal cells are useful to prepare transfected cells that can be immunologically isolated and express heterologous beneficial genes provides the means to correct genetic defects and/or to produce therapeutic proteins. Stromal cells may be isolated with relative ease and isolated stromal cells may be cultured to increase the number of cells available. Stromal cells can be transfected, immunologically isolated and implanted with a high degree of viability into locations that lack direct blood supply such as subcutaneous locations. In some embodiments, stromal cells may immortalized such as by SV40 virus or proteins with transforming properties.

In some aspects of the invention, individuals suffering from genetic diseases and disorders may be treated by supplementing, augmenting and/or replacing defective or deficient genes by providing immunologically isolated stromal cells containing gene constructs that include normal, functioning copies of the deficient gene. This aspect of the invention relates to gene therapy in which the individual is provided with genes for which they are deficient in presence and/or function. The genes provided in the cell therapeutic compensate for the defective gene of the individual. Such genes preferably encode proteins that are secreted.

The stromal cells are transfected and immunologically isolated. In some embodiments, stromal cells are transfected with genes for which the individual to be treated suffers from a complete absence of a non-mutated copy of the gene, or suffers from an absence or insufficient expression of a non-mutated form of the protein. Stromal cells are transfected with a non-mutated copy of the gene in an expressible form. That is, the protein encoded by the transfected gene will be expressed by the stromal cells, preferably as a secreted protein. Examples of diseases, conditions or disorders in which defective genes or insufficient gene expression is causally linked to the disease or symptoms include, but are not limited to, growth hormone deficiency, diabetes, adenine deaminase deficiency, hemophilia A and hemophilia B. Other genetic diseases which may be treated using methods of the invention include: $\alpha_1$-antitrypsin deficiency, Fabray disease, familial hypercholesterolemia, Gaucher's disease, Lesch-Nyhan syndrome, maple syrup urine disease, ornithine transcarbamylase deficiency, phenylketonuria, Sandhoff disease, Tay-Sachs disease and von Willebrand disease. By introducing normal genes in expressible form which encode, growth hormone, insulin, adenine deaminase or an appropriate blood clotting factor, individuals suffering from growth hormone deficiency, diabetes, adenine deaminase deficiency, and hemophilia, respectively, can be provided the means to compensate for genetic defects and eliminate, alleviate or reduce some or all of the symptoms associated with such diseases. Tables IV and V contain partial lists of diseases, conditions and disorders which can be treated using the present invention.

In addition to replacing genes that are defective with functional genes, the invention may also be used to express desired secreted proteins which exert a biologically active therapeutic or prophylactic effect. Such proteins are preferably secreted by the cells. That is, stromal cells may be isolated, furnished with a gene for a desired protein, immunologically isolated and introduced into an individual within whom the desired protein would be produced and exert or otherwise yield a therapeutic effect. This aspect of the invention relates to gene therapy in which therapeutic proteins are administered to an individual. According to these aspects of the invention, the isolated stromal cells are vectors for introducing therapeutic genes into the individual as well as hosts for such genes when the cells are administered to the individual.

In such embodiments, stromal cells are transfected with genes that encode proteins which will have a therapeutic effect when expressed in the individual to be treated. Rather than administering the therapeutic protein directly and at a series of time intervals, the present invention provides a means of administering a therapeutic protein continuously by administering cells which produce the protein. Stromal cells are transfected with a gene that encodes the protein in an expressible form. That is, the protein encoded by the transfected gene will be expressed by the stromal cells, preferably as a secreted protein. Examples of therapeutic proteins include, but are not limited to, obesity factor (Considine, R. V. et al., *J. Clin. Invest.*, 1995, 95, 2986–2988; Arner, P., *N. Engl. J. Med.*, 1995, 333, 382; Emorine, L. et al., *Trends Pharmacol. Sci.*, 1994, 15, 3; Flier, J. S., *Cell*, 1995, 80, 15; Lowell, B. B., et al., *J. Clin. Invest.*, 1995, 95, 923; and Rink, T. J. et al., *Nature*, 1994, 372, 406) granulocyte-macrophage colony stimulating factor, granulocyte colony stimulating factor, erythropoietin, interleukin-2 and interleukin-1 receptor antagonist protein. Tables IV and V contain partial lists of diseases, conditions an disorders which can be treated using the present invention and contain the names of the proteins which can be delivered via a gene construct according to the invention.

In all cases in which a gene construct is transfected into a stromal cell, the heterologous gene is operably linked to regulatory sequences required to achieve expression of the gene in the stromal cell. Such regulatory sequences include a promoter and a polyadenylation signal.

The gene construct is preferably provided as an expression vector which includes the coding sequence for a heterologous protein operably linked to essential regulatory sequences such that when the vector is transfected into the cell, the coding sequence will be expressed by the cell. The coding sequence is operably linked to the regulatory elements necessary for expression of that sequence in the cells. The nucleotide sequence that encodes the protein may be cDNA, genomic DNA, synthesized DNA or a hybrid thereof or an RNA molecule such as mRNA.

The gene construct includes the nucleotide sequence encoding the beneficial protein operably linked to the regulatory elements, and may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The regulatory elements necessary for gene expression include: a promoter, an initiation codon, a stop codon, and a polyadenylation signal. It is necessary that these elements be operable in the stromal cells or in cells that arise from the stromal cells after infusion into an individual. Moreover, it is necessary that these elements be operably linked to the nucleotide sequence that encodes the protein such that the nucleotide sequence can be expressed in the stromal cells and thus the protein can be produced. Initiation codons and stop codon are generally considered to be part of a nucleotide sequence that encodes the protein. However, it is necessary that these elements are functional in the stromal cells or cells that arise from stromal cells. Similarly, promoters and polyadenylation signals used must be functional within the stromal cells or cells that arise from stromal cells. Examples of promoters useful to practice the present invention include but are not limited to promoters that are active in many cells such as the cytomegalic virus promoter, SV40 promoters and retroviral promoters. Other examples of promoters useful to practice the present invention include but are not limited to tissue-specific promoters, i.e. promoters that function in some tissues but not in others; also, promoters of genes normally expressed in stromal cells with or without specific or general enhancer sequences. In some embodiments, promoters are used which constitutively express genes in stromal cells with or without enhancer sequences. Enhancer sequences are provided in such embodiments when appropriate or desirable According to some embodiments, desired genes for transfection into stromal cells are operably linked to the human procollagen I promoter, human procollagen II promoter, and the human procollagen III promoter. In some embodiments, the genes are linked to relatively short 5'-fragments from either the COL1A1 or COL2A1 gene which comprise the promoter together with the some of the 5' translated and/or untranslated sequences of the gene. In some embodiments, the gene to be transfected is operably linked to a sequence that contains a 1.9 kb SphI-HindIII fragment from the 5'-end of the human COL1A1. The fragment contains from −476 bp to +1440 bp of COL1A1 gene and, therefore, includes the promoter (476 bp), exon 1 (222 bp) and most of the intron 1 (1223 bp of a total of 1453 bp). In some embodiments, the gene to be transfected is operably linked to a sequence that contains a fragment from the 5'-end of the human COL2A1. In some embodiments, the fragment contains −4.0 kb of the COL2A1 promoter and the complete COL2A1 gene the one or more exons and introns sequentially from exon 1 to exon 15 and intron 1 to intron 14. Some constructs may be designed as taught in co-pending U.S. Ser. No. 08/184,260 filed Jan. 18, 1994 entitled "Methods of targeting DNA insertion into genome", which is incorporated herein by reference.

Examples of polyadenylation signals useful to practice the present invention includes but are not limited to human collagen I polyadenylation signal, human collagen II polyadenylation signal, and SV40 polyadenylation signal.

In order for exogenous genetic material in an expression vector to be expressed, the regulatory elements must be operably linked to the nucleotide sequence that encodes the protein. In order to maximize protein production, regulatory sequences may be selected which are well suited for gene expression in the desired cells. Moreover, codons may be selected which are most efficiently transcribed in the cell. One having ordinary skill in the art can produce exogenous genetic material as expression vectors which are functional in the desired cells.

It is also contemplated that regulatory elements may be selected to provide tissue specific expression of the protein. Thus, for example, specific promoters may be provided such that the heterologous gene will only be expressed in tissue where the immunologically isolated stromal cells are implanted.

The heterologous protein preferably includes a signal sequence which directs the transport and secretion of the heterologous protein in the stromal cell. The signal sequences is generally processed and removed upon secretion of the mature protein from the cell.

In addition to providing cells with genetic material that either 1) corrects genetic defects in the cells, 2) encodes proteins which are otherwise not present in sufficient quantities and/or functional condition so that the genetic material corrects genetic defects of the individual, and/or 3) encodes proteins which are useful as therapeutics in the treatment or prevention of a particular disease condition or disorder or symptoms associated therewith, genetic material may also be introduced into the stromal cells used in the present invention to provide a means for selectively terminating such cells should such termination become desirable. Such means for targeting cells for destruction may be introduced into stromal cells which are to be otherwise genetically modified as well as those to which no other exogenous genetic material is to be introduced.

According to the invention, isolated stromal cells are furnished with genetic material which renders them specifically susceptible to destruction. For example, the stromal cells may be provided with genes that encode a receptor that can be specifically targeted with a cytotoxic agent. An expressible form of a gene that can be used to induce selective cell death can introduced into the cells. In such a system, cells expressing the protein encoded by the gene are susceptible to targeted killing under specific conditions or in the presence or absence of specific agents. For example, an expressible form of a herpes virus thymidine kinase (herpes tk) gene can be introduced into the cells and used to induce selective cell death. When the exogenous genetic material that includes (herpes tk) gene is introduced into the individual, herpes tk will be produced. If it is desirable or necessary to kill the implanted cells, the drug gancyclovir can be administered to the individual and that drug will cause the selective killing of any cell producing herpes tk. Thus, a system can be provided which allows for the selective destruction of implanted cells.

Those having ordinary skill in the art can identify individuals suffering from genetic diseases such as those listed in Tables IV and V including growth hormone deficiency, diabetes, adenine deaminase deficiency and hemophilia, routinely using standard diagnostic procedures.

Stromal cells may be obtained by removing bone marrow cells from a donor and placing the cells in a sterile container with a plastic surface or other appropriate surface that the cells come into contact with. The stromal cells will adhere to the plastic surface within 30 minutes to about 3 days. After at least 30 minutes, preferably about four hours, the non-adhered cells may be removed and discarded. The adhered cells are stromal cells which are initially non-dividing. After about 2–4 days however the cells begin to proliferate and can be cultured to increase their numbers using standard cell culture techniques.

According to preferred embodiments, stromal cells are cultured in medium supplemented with 2–20% fetal calf serum or serum-free medium with or without additional supplements.

Isolated stromal cells may be transfected using well known techniques readily available to those having ordinary skill in the art. Foreign genes may be introduced into stromal cells by standard methods are employed for introducing gene constructs into cell which will express the proteins encoded by the genes. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA with desired sequences into the stromal cell. In some embodiments, recombinant retrovirus vectors are used to introduce DNA with desired sequences into the stromal cell. In some embodiments, standard $CaPO_4$, DEAE dextran or lipid carrier mediated transfection techniques are employed to incorporate desired DNA into dividing cells. Standard antibiotic resistance selection techniques can be used to identify and select transfected cells. In some embodiments, DNA is introduced directly into cells by microinjection. Similarly, well known electroporation or particle bombardment techniques can be used to introduce foreign DNA into isolated stromal cells. A second gene is usually co-transfected or linked to the therapeutic gene. The second gene is frequently a selectable antibiotic-resistance gene. Transfected cells can be selected by growing the cells in an antibiotic that will kill cells that do not take up the selectable gene. In most cases where the two genes are unlinked and co-transfected, the cells that survive the antibiotic treatment have both genes in them and express both of them.

After isolating the stromal cells, the cells can be administered upon isolation or after they have been cultured.

Isolated stromal cells administered upon isolation are administered within about one hour after isolation. Generally, stromal cells may be administration immediately upon isolation in situations in which the donor is large and the recipient is an infant. It is preferred that stromal cells are cultured prior to administrations. Isolated stromal cells can be cultured from 1 hour to over a year. In some preferred embodiments, the isolated stromal are cultured prior to administration for a period of time sufficient to allow them to convert from non-cycling to replicating cells. In some embodiments, the isolated stromal cells are cultured for 3–30 days, preferably 5–14 days, more preferably 7–10 days. In some embodiments, the isolated stromal cells are cultured for 4 weeks to a year, preferably 6 weeks to 10 months, more preferably 3–6 months.

If the cells are transfected, either 1) isolated, non-cycling stromal cells are first transfected and then administered as non-cycling cells, 2) isolated, non-cycling stromal cells are first transfected, then cultured for a period of time sufficient to convert from non-cycling to replicating cells and then administered, 3) isolated, non-cycling stromal cells are first cultured for a period of time sufficient to convert from non-cycling to replicating cells, then transfected, and then administered, or 4) isolated, non-cycling stromal cells are first cultured for a period of time sufficient to convert from non-cycling to replicating cells, then transfected, then cultured and then administered. In some embodiments, stromal cells are isolated, transfected and immediately administered. It is preferred that stromal cells are cultured prior to transfection and/or administrations. Isolated stromal cells can be cultured from cultured for 3–30 days, in some embodiments 5–14 days, in some embodiments 7–10 days prior to transfection. Transfected stromal cells can be cultured from cultured for 3–30 days, in some embodiments 5–14 days, in some embodiments 7–10 days prior to administration. Isolated stromal cells can be cultured from cultured for 3–30 days, in some embodiments 5–14 days, in some embodiments 7–10 days prior to transfection and upon transfection, additionally cultured for 3–30 days, in some embodiments 5–14 days, in some embodiments 7–10 days prior to administration. In some embodiments, the isolated stromal cells are cultured for 4 weeks to a year, in some embodiments 6 weeks to 10 months, in some embodiments 3–6 months prior to transfection. Transfected stromal cells can be cultured for 4 weeks to a year, in some embodiments 6 weeks to 10 months, in some embodiments 3–6 months prior to administration. In some embodiments, the isolated stromal cells are cultured for 4 weeks to a year, in some embodiments 6 weeks to 10 months, in some embodiments 3–6 months prior to transfection and upon transfection, further cultured for 4 weeks to a year, in some embodiments 6 weeks to 10 months, in some embodiments 3–6 months prior to administration.

Isolated stromal cells may be transfected using well known techniques readily available to those having ordinary skill in the art. In some embodiments, recombinant adenovirus vectors are used to introduce DNA with desired sequences into the stromal cell. In some embodiments, standard $CaPO_4$, DEAE dextran or lipid carrier mediated transfection techniques are employed to incorporate desired DNA into dividing cells. Standard antibiotic resistance selection techniques can be used to identify and select transfected cells. In some embodiments, DNA is introduced directly into cells by microinjection. Similarly, well known electroporation or particle bombardment techniques can be used to introduce foreign DNA into isolated stromal cells.

For administration of stromal cells, the isolated stromal cells are removed from culture dishes, washed with saline, centrifuged to a pellet and resuspended in a glucose solution which is infused into the patient. In some embodiments, bone marrow ablation is undertaken prior to infusion in order to make space in the bone for introduced cells. Bone marrow ablation may be accomplished by X-radiating the individual to be treated, administering drugs such as cyclophosphamide or by a combination of X-radiation and drug administration. In some embodiments, bone marrow ablation is produced by administration of radioisotopes known to kill metastatic bone cells such as, for example, radioactive strontium, $^{135}$Samarium or $^{166}$Holmium (see Applebaum, F. R. et al. 1992 *Blood* 80 (6):1608–1613, which is incorporated herein by reference).

If bone marrow ablation precedes administration of stromal cells, the administration of stromal cells must be accompanied by the administration of non-adherent cells which comprise blood cell precursors necessary for survival. Such non-adherent cells may be saved from the same sample used as starting materials in the isolation of stromal cells and stored or they can be derived from a different sample. In some preferred embodiments, the non-adherent cells are provided by the recipient/patient. Prior to procedures which generate bone marrow ablation, a sample of the patient/recipients bone marrow is obtained and stored. The entire sample may be used or the non-adherent cells may be isolated and used to administer in conjunction with isolated stromal cells. Non-adherent cells administered in conjunction with administration of stromal cells may be administered separately before or after stromal cell administration or may be mixed with isolated stromal cells prior to administration.

Bone marrow ablation is optional. In some embodiments, partial but not complete bone marrow ablation is produced prior to administration of stromal cells. In some embodiments, stromal cells are administered without any bone marrow ablation.

Between $10^7$ and $10^{13}$ cells per 100 kg person are administered per infusion. In some embodiments, between about $1-5\times10^8$ and $1-5\times10^{12}$ cells are infused intravenously per 100 kg person. In some embodiments, between about $1\times10^9$ and $5\times10^{11}$ cells are infused intravenously per 100 kg person. In some embodiments, $4\times10^9$ cells are infused per 100 kg person. In some embodiments, $2\times10^{11}$ cells are infused per 100 kg person.

In some embodiments, a single administration of cells is provided. In some embodiments, multiple administrations are provided. In some embodiments, multiple administrations are provided over the course of 3–7 consecutive days. In some embodiments, 3–7 administrations are provided over the course of 3–7 consecutive days. In some embodiments, 5 administrations are provided over the course of 5 consecutive days.

In some embodiments, a single administration of between $10^7$ and $10^{13}$ cells per 100 kg person is provided, In some embodiments, a single administration of between about $1-5\times10^8$ and $1-5\times10^{12}$ cells per 100 kg person is provided. In some embodiments, a single administration of between about $1\times10^9$ and $5\times10^{11}$ cells per 100 kg person is provided. In some embodiments, a single administration of $4\times10^9$ cells per 100 kg person is provided. In some embodiments, a single administration of $2\times10^{11}$ cells per 100 kg person is provided.

In some embodiments, multiple administrations of between $10^7$ and $10^{13}$ cells per 100 kg person are provided, In some embodiments, multiple administrations of between about $1-5\times10^8$ and $1-5\times10^{12}$ cells per 100 kg person are provided. In some embodiments, multiple administrations of between about $1 \times 10^9$ and $5 \times 10^{11}$ cells per 100 kg person are provided over the course of 3–7 consecutive days. In some embodiments, multiple administrations of $4 \times 10^9$ cells per 100 kg person are provided over the course of 3–7 consecutive days. In some embodiments, multiple administrations of $2 \times 10^{11}$ cells per 100 kg person are provided over the course of 3–7 consecutive days. In some embodiments, 5 administrations of $3-5 \times 10^9$ cells are provided over the course of 5 consecutive days. In some embodiments, 5 administrations of $4 \times 10^9$ cells are provided over the course of 5 consecutive days. In some embodiments, 5 administrations of $1-3 \times 10^{11}$ cells are provided over the course of 5 consecutive days. In some embodiments, 5 administrations of $2 \times 10^{11}$ cells are provided over the course of 5 consecutive days.

Stromal cells in diffusion chambers are described in Benayahu, D. et al. (1989) *J. Cell Physiol.* 140:1–7 and Mardon, H. J. et al. (1987) *Cell Tissue Res.* 250:157–165, which are both incorporated herein by reference.

After introducing the gene construct into the stromal cells, the cells can be immunologically isolated immediately or after they have been cultured Stromal cells can be implanted after they are immunologically isolated. Stromal cells may be immunologically isolated by any number of well known methods using readily available starting materials and/or devices. Stromal cells may be microencapsulated using many such microencapsulation protocols including those disclosed, for example, in U.S. Pat. No. 4,391,909, U.S. Pat. No. 4,806,355, U.S. Pat. No. 4,942,129, and U.S. Pat. No. 5,334,640.

Stromal cells may be administered in chambers with diffusible membranes or encapsulated in microbeads. In another embodiment, the stromal cells are contained in hollow fibers such as those available from Amicon, Inc. (Beverly Mass.). These fibers are used for example to make cartridges for dialysis. One end can be pulled out from under the skin and reduced in size if dosages of the protein made by the cells are to be reduced. The surface area of the fibers is very high. Further, cells in the fiber can be flushed out and replaced periodically. Hollow fibers are described on pages 50–51 of Amicon, Inc. Publication No. 323 which is incorporated herein by reference.

Similarly, incorporation of transfected stromal cells in biocompatible matrices will allow for secretion of beneficial protein to the individual while maintaining the cells in an immunologically isolated condition. Examples of biocompatible matrices are disclosed, for example, in U.S. Pat. No. 4,902,295 and U.S. Pat. No. 4,997,443. In some embodiments, transfected stromal cells are immunologically isolated by encasing them within tissue implant systems that are membrane assemblies. That is, cells are maintained in containers that include at least one porous membrane. The cells within the membrane assembly are immunologically isolated while beneficial proteins may be made available to the S individuals by passing through the membrane. Implant devices which are membrane assemblies, include, but are not limited to, those described in U.S. Pat. No. 5,314,471 and U.S. Pat. No. 5,344,454. According to one embodiment of the invention, an implant device is provided which comprises two ring assembles. Each ring assembly comprises a circular plastic ring and a 0.3 micron MILLI-PORE™ membrane covering the area of the circle. Transfected stromal cells are disposed between the two ring assembly which are connected to each other at the circumference. The constructed implant device is preferably implanted subcutaneously.

In some preferred implant devices, $10^4$ to $10^{11}$ cells are provided.

Immunologically isolated cells may be implanted subcutaneously or intraperitoneally. Alternatively, they may be attached or otherwise implanted adjacent to organs and tissues to which the beneficial protein is preferably delivered. In preferred embodiments, implant devices are implanted subcutaneously or intraperitoneally.

The invention is particularly useful to treat those diseases, disorder and conditions which require relatively small quantities of protein, most preferably secreted protein. Examples include growth factor, obesity factor and factor IX which each require very small amount of protein in order to function. Tables IV and V contain partial lists of diseases, conditions and disorders which can be treated using the present invention.

It is preferred that stromal cells are cultured prior to immunological isolation. Stromal cells can be cultured from 1 hour to over a year. In some preferred embodiments, the stromal cells are cultured for a period of time sufficient to allow them to convert from non-cycling to replicating cells. In some embodiments, the stromal cells are cultured for 3–30 days, preferably 5–14 days, more preferably 7–10 days. In some embodiments, the stromal cells are cultured for 4 weeks to a year, preferably 6 weeks to 10 months, more preferably 3–6 months.

In preferred embodiments, cells are either 1) isolated, non-cycling stromal cells that are first transfected and then immunologically isolated, then implanted as non-cycling cells, 2) isolated, non-cycling stromal cells that are first transfected, then cultured for a period of time sufficient to convert from non-cycling to replicating cells, then immunologically isolated and then implanted, 3) isolated, non-cycling stromal cells that are first cultured for a period of time sufficient to convert from non-cycling to replicating cells, then transfected, then immunologically isolated and then implanted, or 4) isolated, non-cycling stromal cells that are first cultured for a period of time sufficient to convert from non-cycling to replicating cells, then transfected, then cultured, then immunologically isolated and then implanted. In some embodiments, stromal cells are isolated, transfected, immunologically isolated and implanted. It is preferred that stromal cells are cultured prior to and after transfection. Isolated stromal cells can be cultured from cultured for 3–30 days, in some embodiments 5–14 days, in some embodiments 7–10 days prior to transfection. Transfected stromal cells can be cultured from cultured for 3–30 days, in some embodiments 5–14 days, in some embodiments 7–10 days prior to administration. Isolated stromal cells can be cultured from cultured for 3–30 days, in some embodiments 5–14 days, in some embodiments 7–10 days prior to transfection and upon transfection, additionally cultured for 3–30 days, in some embodiments 5–14 days, in some embodiments 7–10 days prior to administration. In some embodiments, the isolated stromal cells are cultured for 4 weeks to a year, in some embodiments 6 weeks to 10 months, in some embodiments 3–6 months prior to transfection. Transfected stromal cells can be cultured for 4 weeks to a year, in some embodiments 6 weeks to 10 months, in some embodiments 3–6 months prior to implantation. In some embodiments, the isolated stromal cells are cultured for 4 weeks to a year, in some embodiments 6 weeks to 10 months, in some embodiments 3–6 months prior to transfection and upon transfection, further cultured for 4 weeks to a year, in some embodiments 6 weeks to 10 months, in some embodiments 3–6 months prior to implantation.

Another aspect of the present invention relates to methods of treating patients who are suffering from a disease, disorder or condition characterized by a bone or cartilage defect. The method comprises the steps of identifying an individual with a bone or cartilage defect, obtaining a bone marrow sample from a normal, matched, syngeneic donor, and, administering said bone marrow sample to the patient by intravenous infusion.

As stated above, the bone marrow sample for transplantation may be derived from a matched donor. Those having ordinary skill in the art can readily identify matched donors using standard techniques and criteria.

Bone marrow samples for transplantation may be obtained from matched donors by standard techniques. In some embodiments, bone marrow ablation is undertaken prior to infusion in order to make space in the bone for introduced cells. Bone marrow ablation may be accomplished by X-radiating the individual to be treated, administering drugs such as cyclophosphamide or by a combination of X-radiation and drug administration In some embodiments, bone marrow ablation is produced by administration of radioisotopes known to kill metastatic bone cells such as, for example, radioactive strontium, $^{135}$Samarium or $^{166}$Holmium (see Applebaum, F. R. et al. 1992 Blood 80(6):1608–1613, which is incorporated herein by reference).

Bone marrow ablation is optional. In some embodiments, partial but not complete bone marrow ablation is produced prior to bone marrow transplantation. In some embodiments, bone marrow is administered without any bone marrow ablation.

It is preferred that the number of cells used in bone marrow transplantation for treating bone and cartilage disease exceed that which is normally used for other treatments. Between 3 to 10 times the normal bone marrow dosage per 100 kg person are administered per infusion.

In some embodiments, a single administration of cells is provided. In some embodiments, multiple administrations are provided. In some embodiments, multiple administrations are provided over the course of 3–7 consecutive days. In some embodiments, 3–7 administrations are provided over the course of 3–7 consecutive days. In some embodiments, 5 administrations are provided over the course of 5 consecutive days.

In some embodiments, a single administration of between $10^7$ and $10^{13}$ cells per 100 kg person is provided, In some embodiments, a single administration of between about $1-5\times10^8$ and $1-5\times10^{12}$ cells per 100 kg person is provided. In some embodiments, a single administration of between about $1\times10^9$ and $5\times10^{11}$ cells per 100 kg person is provided. In some embodiments, a single administration of $4\times10^{11}$ cells per 100 kg person is provided. In some embodiments, a single administration of $2\times10^{11}$ cells per 100 kg person is provided.

In some embodiments, multiple administrations of between $10^7$ and $10^{13}$ cells per 100 kg person are provided, In some embodiments, multiple administrations of between about $1-5\times10^8$ and $1-5\times10^{12}$ cells per 100 kg person are provided. In some embodiments, multiple administrations of between about $1\times10^9$ and $5\times10^{11}$ cells per 100 kg person are provided over the course of 3–7 consecutive days. In some embodiments, multiple administrations of $4\times10^9$ cells per 100 kg person are provided over the course of 3–7 consecutive days. In some embodiments, multiple administrations of $2\times10^{11}$ cells per 100 kg person are provided over the course of 3–7 consecutive days. In some embodiments, 5 administrations of $3-5\times10^9$ cells are provided over the course of 5 consecutive days. In some embodiments, 5 administrations of $4\times10^9$ cells are provided over the course of 5 consecutive days. In some embodiments, 5 administrations of $1-3\times10^{11}$ cells are provided over the course of 5 consecutive days. In some embodiments, 5 administrations of $2\times10^{11}$ cells are provided over the course of 5 consecutive days.

EXAMPLES

Example 1

Cells from a transgenic mouse line that expresses a human mini-gene for collagen I in a tissue-specific manner were used to see whether precursor mesenchymal cells from marrow that are expanded in culture can serve as long-term precursors of bone and other connective tissues after intravenous infusion into irradiated mice. The marker gene consisted of an internally deleted mini-gene for the human proα1 (I) chain of procollagen I that caused synthesis of shortened proα1 (I) chains (Khillan, J. S. et al., *J. Biol. Chem.* 266:23373–23379 (1991); Pereira, R. et al., *J. Clin. Invest.* 91:709–716 (1983); and Sokolov, S. P. et al., *Biochemistry* 32:9242–9249 (1993)) which are incorporated herein by reference. Cells expressing the gene were obtained from a line of transgenic mice in which the copy number of the human mini-gene relative to the endogenous mouse gene was about 100 to 1, and the steady-state levels of mRNA from the human mini-gene relative to mRNA from the endogenous mouse gene was about 0.5:1 in most tissues.

Donor cells from marrow partially enriched for mesenchymal precursors were prepared by standard protocols (Friedenstein, A. J. et al., *Exp. Hemat.* 4:267–274 (1976); Castro-Malaspina, H. et al., *Blood* 56:289–301 (1980); Piersma, A. H. et al., *Exp. Hematol* 13:237–243 (1985); Simmons, P. J. and Torok-Storb, B., *Blood* 78:55–62 (1991); Beresford, J. N. et al., *J. Cell. Sci.* 102:341–351 (1992); Liesveld, J. L. et al., *Blood* 73:1794–1800 (1989); Liesveld, J. L. et al., *Exp. Hematot* 19:63–70 (1990); and Bennett, J. H. et al., *J. Call. Sci.* 99:131–139 (1991)) which are incorporated herein by reference. Briefly, the ends of long bones from the transgenic mice were cut, and the marrow was extracted with a pressurized syringe filled with α-MEM (Sigma) containing 10% fetal bovine serum (Atlanta Biologicals). About $10^7$ nucleated cells were plated onto 175 cm$^2$ plastic culture flasks in 25 ml of α-MEM containing 10% fetal bovine serum. After 4 h, the non-adherent cells were discarded by replacing the medium. Foci containing two to four fibroblast-like cells appeared in 2 to 3 days, and the foci grew to near-confluent colonies in about 1 wk. The yield was about $10^7$ cells per flask after trypsin digestion. By phase-contrast microscopy, most of the cells were fibroblast-like, but a few macrophages and adipocytes were also seen.

About $10^5$ of the cultured adherent cells were mixed with $6\times10^5$ non-adherent cells obtained by incubation of marrow from normal mice for 4 h on 175 cm$^2$ flasks under the same conditions used for the initial isolation of the adherent cells. The mixture of about $7\times10^5$ cells in 0.2 to 0.4 ml of α-MEM and 10% fetal bovine serum was injected into the tail vein of each recipient mouse.

Eight-week old mice from the same inbred FVB/N line were prepared to receive the donor cells by irradiation with a $^{137}$Cu irradiator (Atomic Energy of Canada, Ltd.). The unit had a dose rate of 116 cG/min with a parallel opposed beam configuration. Each animal received 9.0 Gy in two fractions with a 4 h interval (4.5 Gy+−4.5 Gy) (O'Hara, M. D. et al., *Exp. Hemat* 19:878–881 (1991)). One to 2 h after the second radiation fraction, the mixture of marked adherent cells and normal non-adherent cells was injected intravenously. Control irradiated mice that did not receive a cell infusion died after 10 to 13 days of marrow failure.

To follow the fate of the donor cells, two PCR assays for the human COL1A1 mini-gene and the mouse endogenous COL1A1 gene were developed. With a two-primer assay, the values for the ratio of the human to mouse gene were linear over a range of $10^{-4}$ to about $10^{+1}$ and, therefore, of about $10^{-6}$ to $10^{-1}$ donor cells per recipient cell. With the three-primer assay, the values were linear over a range of about $10^{-3}$ to $10^{+2}$ and, therefore, about $10^{-5}$ to 1 donor cell per recipient call.

Assays of irradiated mice after one day indicated only trace amounts of the donor cells in marrow, spleen, bone, lung or brain (Table 1). Slightly higher levels were seen at seven days. At 30 days and 150 days, progeny of the donor cells accounted for 2.0 to 12% of the cells in marrow, spleen, bone and lung (Table 1). At 150 days, they also accounted for 1.5 to 5.0% of the cells in xiphoid cartilage that was dissected free of any mineralized or fibrous tissue under a microscope. Although the mean values appeared to show a decrease between 1 and 5 months, there was no statistically significant decrease in the combined values for marrow, spleen, bone and lung between these two time periods (Table 1). Assays of non-irradiated mice revealed only very low levels of the donor cells at the same time points (<0.0001 to 0.05%). PCR in situ assay of tissue sections of lung demonstrated that progeny of the donor cells were evenly distributed in the parenchyma of both alveoli and bronchi.

To confirm that progeny of the donor calls were present in cartilage, chondrocytes were isolated from xiphoid and articular cartilage by digestion at 370° C. overnight with 0.5 mg/ml bacterial collagenase (Sigma) in DMEM. PCR assays indicated that progeny of the donor cells accounted for 2.5% of the isolated chondrocytes.

To determine whether the donor cells became functional mesenchymal cells in the tissues they populated, tissues from the recipient mice were assayed by RT-PCR for expression of the human mini-gene for collagen I contained in the donor cells. In three mice assayed at 150 days, the mini-gene was expressed in bone), a tissue in which over half the protein synthesized in collagen I. The expression in bone was confirmed by a similar assay on bone cells isolated from femur and cultured for 1 wk. Expression of the mini-gene for collagen I was more variable in marrow, spleen and lung, tissues in which the rate of collagen I synthesis is less than in bone. As expected, the mini-gene was not expressed in cartilage, a tissue in which about half the protein is synthesized in collagen II but in which there is no synthesis of collagen I. The mini-gene for collagen I was also not expressed in cultures of chondrocytes from the recipient mice that contained the marker gene and that synthesize collagen II but not collagen I.

Earlier reports have shown that assays of the cells with cytochemical markers or for mRNAs indicated that the cells synthesized collagen I, collagen III, fibronectin, alkaline phosphatase and osteopontin, but did not have features characteristic of macrophages, granulocytes, T lymphocytes, B lymphocytes or endothelial cells. The results here demonstrate that after intravenous injection into irradiated mice, the expanded cultures of adherent cells efficiently populate several connective tissues. The results also demonstrate that the cells serve as true precursor cells for these tissues, since they expressed the marker gene for collagen I in a tissue-specific manner, and they were diffusely incorporated into the mesenchymal parenchyma of lung.

Example 2
Conditions for Isolation and Culture of MSCs

Conditions for culture of MSCs so that they expand but retain the stem-cell-like phenotype have been studied. Table I shows that co-culture of MSCs with pieces of bone increased the number of cells obtained after 1 wk. At the same time, co-culturing with bone decreased the alkaline phosphatase (APase) levels in the cells, an observation suggesting that the cells did not differentiate into osteoblasts. Also, there was a decrease in the levels of tartrate-resistant acid phosphatase (TRAP), an observation suggesting that the cells did not differentiate into osteoclasts. Similar effects were observed with secondary cultures of the MSCs. Therefore, the results suggest that co-culturing with pieces of bone may provide improved conditions for expansion of MSCs. Also, the medium of cultured bone pieces may be an important source of cytokines and growth factors for expansion of MSCs in culture.

In related experiments, it has been found that secondary cultures of MSCs can be maintained for long periods of time. MSCs can be passed in culture for over 4 months by trypsinization and re-plating. The cells are remarkably stable in stationary phase cultures. In one experiment, stationary cultures remained viable for over 4 months with re-feeding about once per wk. In another experiment, the cells remained viable when, through an oversight, they were left in an incubator without re-feeding for 1 month.

Stable Transfection of MSCs with a Retrovirus Vector

To obtain virus for infection of MSCs, the LNCZ retroviral vector (Miller, A. D. and Rosman, G. J. (1989) *BioTechniques* 7, 980–990 which is incorporated herein by reference) was modified so that the promoter for cytomegalovirus (PCMV) drove expression of the lacZ gene (FIG. 1). The vector was stably transfected into an amphotropic murine packaging cell line (PA317). Constitutive virus producer clones were isolated by G418 selection, and supernatant from the clones was used for infection of MSCs. Primary cultures MSCs (3 days old) were infected for three successive days with fresh supernatant from the producer line with the highest titer. Staining of the cells 5 days later indicated that about 15–200% of the cells typically expressed the lacZ gene. Several cultures of the infected cells were placed under selection with G418 (0.44 µg/ml active concentration) for 5 days. Most of the cells recovered continued to express the lacZ gene. Modifications of LNCZ were also constructed so that expression of the lacZ gene is driven by the promoter of the COL1 A1 gene and the promoter of the COL2 A1 gene (pCOL2A1). Expression of the lacZ gene was successfully obtained in primary cultures of MSCs with both constructs.

Replacement of Bone Cells in Transgenic Mice with Normal MSCs

MSCs from normal mice were infused into the transgenic mice that expressed high levels of the mutated COL1 A1 gene (Tables II and III). One month after the infusion of normal MSCs into the osteoimperfecta (OI) mice (Table II), progeny of the donor cells accounted for 10 to 45% of the bone cells in recipient mice that had been irradiated with a maximally tolerated dose of X-ray (700 centi-Gray or cGy). Similar values were obtained with mice irradiated with one-half of the maximally tolerated dose of X-ray (350 cGy). However, reducing the dose to one-quarter (175 cGy) reduced the values in four mice to 0%, 5%, 10% and 40%. Similar results were obtained when OI transgenic mice were infused with large numbers of whole marrow cells from which MSCs were not removed (Table III).

In five recipient mice in which the synthesis of proα1(1) chains was examined (Tables II and III), the replacement of the recipient's bone cells by normal donor MSCs was accompanied by an increase in the ratio of normal proα1(1) chains to mutated proα1(1) chains in bone. Hence, the replacement by normal cells was accompanied by the expected changes at the protein level.

Example 3
Long-Term Expression of the Human Genes for hGH, Factor IX or Ob in Stably Transfected MSCs MSCs are isolated from mice and cultured under the conditions described in Pereira, R. F., et al. (1995) *Proc. Natl. Acad. Sci. USA* 92, 4857–4861, which is incorporated herein by reference. MSCs are infected with retroviral vectors or transfected with naked DNA to obtain clones that express the genes for human growth hormone (hGH), the human obesity protein (Ob), or the gene for human factor IX. Because a lacZ gene has been successfully introduced into mouse MSCs with a retroviral vector, variants of the same vector are used. At the same time, MSCs are stably transfected with electroporation (Andreason, G. L and Evans, G. A. (1988) *BioTechniques* 6, 650–660 and Toneguzzo, F., et al. (1986) *Mol. Call. Biol.* 6, 703–706, which are incorporated herein by reference), lipofectamine and nuclear injection (Mercer, W. E., et al. (1992) In: *Antisense Strategies, Ann. N.Y. Acad. Sci. Biol.* 660, 209–218, which is incorporated herein by reference) so that larger endogenous genes can be used. Further, some of the potential disadvantages of retroviruses are avoided using alternative introduction methodology.

Standard conditions for isolation and culture are: Whole marrow is obtained from the tibias and femurs of 6- to 10-wk old FVB/N mice by cutting the ends of the bones and extruding the marrow with a syringe that contains 1 to 2 ml of ice-cold αMEM and 10% fetal bovine serum (FBS). The pooled marrow cells are dispersed by gentle shaking and counted in an automatic counter (Coulter model ZM). From $5 \times 10^6$ to $5 \times 10^7$ nucleated cells in 25 ml of α-MEM and 10% FBS are plated onto 75-cm$^2$ culture flasks. After 4 h or 3 days, the non-adherent cells are removed by replacing the medium. The adherent cells are expanded as primary cultures for 10 to 12 days with a re-feeding about every 4 days. The cells are recovered by digestion with 0.25% trypsin and 1 to 5 mM EDTA for 5 min at 37° C. followed by gentle scraping. The cells are diluted with α-MEM with 10% FBS and replated at a density of from $3 \times 10^4$ to $1 \times 10^5$ cells per 9.5 cm$^2$ in 6-well plates. Under these conditions, the doubling time of the cells is 19 to 22 hours. The secondary cultures are re-fed about every 4 days, and passed by trypsinization and replating under the same conditions.

Preparation of Gene Constructs

The retrovirus vector LNCX is used As the parent construct. Convenient cloning sites in the construct are used to prepare the modified constructs pRSV-lacZ, pCMV-lacZ, pCOL1-/LacZ and pCOL2-lacZ (FIG. 1). The pCOL1 promoter is a 1.4 kb fragment that contains 476 bp of the promoter, the first exon and most of the first intron of the human COL1A1 gene. The promoter has been shown in transgenic mice to express a promoterless form of the COL2A1 gene in a highly tissue specific and developmental specific manner (Sokolov, B. P., et al. (1995) *J. Biol. Chem.* 270, 9622–9629 which is incorporated herein by reference). The COL2A1 promoter is a 1 kb fragment from the human COL2A1 gene (Ala-Kokko, L., et al. (1991) *J. Biol. Chem.* 266, 14175–14178 which is incorporated herein by reference) that confers tissue-specificity of expression (Bradham, D. M., et al. (1994) *J. Cell Physiol.* 158, 61–68 which is incorporated herein by reference). The lacZ gene is replaced with the hGH gene (Nichols Laboratories); the OB gene (Considine, R. V., et al. (1995) *J. Clin. Invest.* 95, 2986–2988, which is incorporated herein by reference) or the human factor IX gene (Genetic Therapy, Inc.)

Use of the Retrovirus Vector

Retrovirus Producer Cell Lines

To establish producer cell lines, amphotrophic retrovirus packaging murine cells PA317 were used. The cells were transfected at 20% confluency in 100 mm dishes by the calcium phosphate precipitation procedure (Promega) using 15 µg of plasmid DNA that was linearized by digestion with ScaI that cuts in the pBR322 region of the retrovirus vector. One day post-transfection G418 (GIBCO/BRL) was added to the medium at an active concentration of 1 mg/ml. Neomycin-resistant colonies appeared at 7 to 10 days of selection and were isolated by cloning with mechanical rings. The clones were expanded and individual clones were tested for the ability to express lacZ by direct staining of duplicate wells. The titer of the virus produced by the positive cells was assayed by single addition of 50 µl of medium to HT-1080 human tumor cells grown to 200% confluency in 6-well microliter plates with 3 ml medium per well and in the presence of 4 µg/ml of polybrene. The titer was assayed by determining the number of HT-1080 cells that stained positively for expression of the lacZ gene. Typically, the titer was $1 \times 10^5$ to $1 \times 10^6$.

Retrovirus Infection of Mouse MSCs

Primary cultures of mouse MSCs were prepared as described above. After 3 days, the non-adherent marrow cells were discarded and fresh medium added. The cells were then infected with the retrovirus in the presence of 4 µg/ml of polybrene by addition of ¼ vol of fresh supernate medium from stably transfected producer cells that had the highest titer of virus production. The infection was repeated on two additional successive days. The cells were then either stained directly for lacZ expression or divided into larger dishes and placed under selection with 0.4 µg/ml of G418 (active concentration). About 15 to 20% of primary cultures were positive for lacZ and most of the cells that survived G418 selection were positive for lacZ.

Lipofectamine Transfection

Primary cultures of MSCs were grown for 10 days in (α-MEM containing 10% FBS). After trypsinization and light scraping, the cells were seeded in a 6-well plate at a density of $10^5$ cells per well. The cells were grown for 2 days, then washed 2 times with PBS and incubated with a DNA-lipofectamine complex. The DNA-lipofectamine complex was prepared as follows: 6 µl of lipofectamine (GIBCO/BRL) were mixed with 1 µg of LINCZ DNA in 200 µl of α-MEM, incubated at room temperature for 30 min, and added to one well of a 6-well plate containing MSCs in 800 µl α-MEM. After 6 h incubation at 37° C., the DNA-lipofectamine complex was replaced with 2 ml of α-MEM containing 10% FBS. The cells were stained for lacZ or placed under G418 selection after 18 h incubation in FBS-containing medium. Positive clones were obtained, but they grew slowly, apparently because the cell density was too low after the G418 selection. To circumvent this situation, three different strategies can be used: (a) cells are plated at higher densities; (b) co-culture cell culture inserts will be placed over surviving clones early in the selection process and place fresh MSCs or pieces of bone in the inserts (see Table 1) on a daily basis to provide the necessary cell factors to stimulate growth; (c) at the time that selection with G418 has killed many of the non-transfected calls, the cultures are reseeded with MSCs that have been infected with a variant of the retrovirus LNCX (FIG. 1) in which the lacZ gene is replaced with a selectable gene for thymidine kinase. Therefore, the MSCs stably transfected with retrovirus are used to provide the necessary cytokines, growth factors, and cell interactions required for the initial growth of the transfected MSCs during selection in G418. We can then remove the cells infected with the retrovirus by negative selection with gangcyclovir.

Delivery Methods

Nuclear Injections

Nuclear injections are highly efficient as a means of transfecting some cells. Cells were plated in 60-mm dishes containing a 22×22 mm coverslip marked with a circle to delineate the area for microinjection. Cells were incubated in medium containing 0.1% CS for 5 days to induce growth arrest before microinjection. Under these conditions between 8 and 15% of the cells incorporated [$^3$H]thymidine during continuous labeling for 24 h between days 5 and 6. Microinjection was performed using a Zeiss Axiovert inverted-microscope equipped with an Eppendorf microinjector and micromanipulator using commercially purchased glass-capillary femtotips (Eppendorf). All cells within a delineated area of the coverslip (usually 150–200) were microinjected into the nucleus with DNA at concentrations ranging from 0.01–10 μg/μl in 10 mM Tris buffer (pH 7.6). The injected cells will be expanded and assayed as described above.

Electroporation

MSCs are treated with 0.25% trypsin and 1 to 5 mM EDTA for 5 min at room temperature and then harvested by scraping. The cells are pelletted by centrifugation at 4,000×g for 10 min, and then are washed twice by resuspending the pellet in ice cold PBS (pH 7.4). MSCs are resuspended at 2×10$^6$ cells per 0.8 ml and aliquoted into an electroporation cuvette (0.4 cm gap). The cells are incubated 10 min on ice, DNA is added to the suspension (5–50 μg), and the cells are chilled for an additional 10 min. The cell suspension is then electroporated using a commercial instrument (BioRad Gene Pulser; model 1652076) at an empirically determined field strength which yields the greatest percentage of cells that retain the exogenously added DNA. To determine the appropriate field strength for MSCs, titrations have been performed ranging from 0.25–2.5 kv/cm. Electroporation efficiency was monitored by introducing a lacZ gene (LNCZ vector) and then staining cells 48 to 72 h after electroporation.

Assays hGH

Expression of the hGH gene is monitored by assaying medium from clones of calls grown in 6-well microliter plates with an enzyme linked immunoabsorbent assay with a commercially available kit (GIBCO/BRL). In this assay, 0.1 ml of 2× diluent buffer is added per well of a microliter plate. After 5 min, 0.1 ml of test sample is added and the plate incubated at 37° C. for 30 min. The wells are washed 5 times and 0.2 ml of primary antibody added per well. The samples are incubated at 37° C. for 30 min, and washed 5 times. Then 0.2 ml of substrate buffer containing O-phenylenediamine substrate is added. Samples are incubated at room temperature for 30 min and the reaction stopped by addition of 0.1 ml of 2 N sulfuric acid. The absorbance of the sample is assayed at 490 nm.

Ob Protein

Cells are assayed for expression of the OB gene with a protein radioimmunoassay of cell medium. The primary antibody for human OB protein was raised in rabbits against recombinant protein synthesized in an E. coli expression system and purified to homogeneity. The human protein is highly homologous to the mouse and, therefore, anti-human antibodies should cross-react with the mouse protein. If they do not, the short mouse cDNA (619 nt) is expressed in E. coli, the protein is purified and antibodies are prepared. Alternatively, synthetic peptides with the mouse sequence are purchased and use these to prepare antibodies. For the assay, recombinant human Ob protein was radiolabeled with –$^{125}$Iodine by the Bolton-Hunter method followed by gel filtration purification using Sephadex G-25. The specific activity obtained was –30 μCi/μg. Samples of assay (0.2 ml) were preincubated with primary antiserum (1:2000 dilution) in phosphate buffered saline containing 0.1% Triton X-100 for 16 h at 40° C. in a total Volume of 0.4 ml. $^{125}$I-Ob protein (–30,000 cpm carried in 100 μl) was then added and the incubation continued for an additional 24 h. The bound Ob protein (12±1%; nonspecific binding 1.4±0.1%) was immunoprecipitated by addition of 0.1 ml sheep anti-rabbit IgG serum (Antibodies, Inc., Davis, Calif.), 0.1 ml normal rabbit serum (GIBCO/BRL, Gaithersburg, Md.), and 0.1 ml of 10% polyethylene glycol. The tubes were centrifuges for 15 min (2200 rpm), and unbound label decanted and the pellet counted in a Packard 5000 gamma counter (Downers Grove, Ill.). The concentration of Ob protein in unknown samples was calculated using Rodbard's unweighted four parametric logistic model. The limit of detection of this assay is 0.39 ng/ml. The intra-assay variance is 11.6% at 12 ng/ml with an interassay variance of 20.8% at 13.1 ng/ml.

Human Factor IX

Expression of the gene for factor IX will be assayed with a commercially available ELISA (American Bioproducts Company) under conditions similar to those used for the hGH assay (above). As reported by Smith et al. (74), the standard curve ranged from 1–50 ng/ml$^{-1}$ and the limit of sensitivity was 1 ng/ml–$^1$. The assay did not cross-react with mouse factor IX.

Example 4

Sustained Expression of the Three Genes at Physiologically Important Levels by Systemic Infusion of Stably Transfected MSCs into Mice Experiments with the OI transgenic mice (Tables II and III) have demonstrated that cultured MSCs can serve as stem-cell-like precursors of bone, cartilage and other mesenchymal tissues after systemic infusion. Therefore, MSCs expressing hGH, the Ob protein or factor IX are infused into irradiated and nonirradiated mice to evaluate sustained expression of the genes in vivo.

Infusion of MSCs

Initially, MSCs are infused into mice under conditions such as those described in Table II (3-week old mice: 300 or 700 Gray irradiation; intraperitoneal injection; 1×10$^6$ MSCs; and 2×10$^8$ whole marrow cells). In addition, intravenous infusion is compared to intraperitoneal; and lower levels of X-ray irradiation are employed. Also, the cells are infused into embryos by Cesarean section. In preliminary trials, 50 μl of 5×10$^4$ES were injected into the amnion of seven 13-day embryos; 6 of 7 were delivered as viable pups. Therefore, intrauterine injection of MSCs is feasible.

Growth Curves

Effective in vivo expression of hGH should increase the growth rate of mice and expression of the Ob protein should induce starvation. Therefore, the weight and size of the treated mice and of control littermates are monitored.

Assays for Gene Expression

Blood is obtained from the retro-orbital plexus of mice at 1 wk. 1 month, 3 month, 5 month, 10 month, and 20 month after infusion of the MSCs. hGH and factor IX are assayed by ELISA, and the Ob protein is assayed with a radioimmune assays. In addition, if measurable increases in human factor IX are obtained with ELISA, the procedure described in Smith, T. A. G., et al. (1993) *Nature Genet.* 5 397–402, which is incorporated herein by reference, to assay biologically active human factor IX. In this procedure, human factor IX was first captured in a microtiter well with the monoclonal antibody, BGIX1, and then activated by factor XIa. The active factor IX, in combination with factor VIII, converted factor X to Xa. Factor Xa cleaved the chromogenic substrate, S2765, yielding a yellow product. BGIX1-coated microtiter plates and Factor VIII were purchased from Elcatech, Inc. (Winston-Salem, N.C.). Factor Xia was purchased from Enzyme Research Labs, Inc. (South Bend, Ind.). Factor X, phospholipid solution, S-2765, and the thrombin inhibitor, 1–2581, were purchased from Kabi Pharmacia Hepar, Inc. (Franklin, Ohio). Four buffers were prepared: A, 50 mM Tris, 150 mM NaCl, 1% BSA, pH 7.5; B, 150 mM Tris, 5 mM $CaCl_2$1 10 mg/ml$^{-1}$ gelatin, pH 7.6; C, 50 mM Tris, 10 mM $CaCl_2$ pH 7.5; D, 50 mM Tris, 150 mM NaCl, pH 8.4. The Factor VIII/X reaction mix was prepared fresh by mixing equal quantities of the following stocks: factor VIII, 5 U ml$^{-1}$ in buffer A; factor X, 1 U ml$^{-1}$ in buffers; 1–2581, 34 µg/ml$^{-1}$ in buffer A; $CaCl_2$, 25 mM in water; and phospholipid. Plasma samples were diluted in buffer A and 100 µl were added to each microtiter well. The plate was incubated for 90 min au room temperature and then washed five times with buffer B. 100 µl of Factor XIa (2 µg/ml$^{-1}$ in buffer C) were added to each well. After 30 min at 37° C., 100 µl of S2765 (0.5 mM in buffer D) were added to each well and the plate was incubated for 10 min at room temperature before the reaction was stopped by adding acetic acid to a final concentration of 10%. Absorbances at 405 nm were determined with a Bio-Rad microplate reader. The standard curve, prepared with dilutions of human normal pooled plasma, was linear from 3–25 ng/ml$^{-1}$. The assay did not cross react with mouse factor IX. Factor IX, levels of 250 ng per ml or 5% of normal are generally considered therapeutic and 100 to 150 ng/ml are considered beneficial.

Example 5

Sustained Expression of the Genes at Physiologically Important Levels by Placing the MSCs in Subcutaneous Diffusion Chambers Cells implanted in subcutaneous diffusion chambers have at least two distinct advantages for therapy of patients: (a) immune responses are circumvented; and (b) when implanted in capsules in mice (Benayahu, D., et al. (1989) *J. Cell Physiol.* 140, 1–7, which is incorporated herein by reference), rats (Mardon, H. J., et al. (1987) *Cell Tissue Res.* 250, 157–165, which is incorporated herein by reference) or rabbits (Friedenstein, A. J., et al. (1987) *Cell Tissue Kinet.* 20, 263–272, which is incorporated herein by reference), they survive for at least 6 wks (Wakitani, S., et al. (1994) *J. Bone and J.T. Surgery* 76A, 579–592, which is incorporated herein by reference), apparently because they persist as bone, fibrous tissue or cartilage that does not require vascularization (Benayahu, D., et al. (1989) Supra, Mardon, H. J., et al. (1987) Supra, Owen, M. and Friedenstein, A. J. (1988) In: *Cell and Molecular Biology of Invertebrate Hard Tissues*, Wiley Chicester, CIBA Foundation Symposium, 136, 42–60, which is incorporated herein by reference, and Friedenstein, A. J., et al. (1987) Supra).

Preparation of Chambers

Diffusion chambers are assembled from commercially available components (Millipore Corp.) and used as described in previous reports (Benayahu, D., et al. (1989) Supra, Mardon, H. J., et al. (1987) Supra,). Briefly, membrane filters with 0.3 µm pore size are glued to one side of each of two plastic rings with acryloid glue. The two rings are then glued together to form a chamber, the dimensions are 9 mm inner diameter and 2 mm thick with a volume of about 127 mm$^3$. From $10^4$ to $10^7$ MSCs are inoculated into the chambers through a hole in one ring and the hole sealed with a tapered plastic plug coated with glue. The chambers are implanted into mice either subcutaneously on the back or intraperitoneally under anesthesia. Initially, one or more chambers are inserted into freshly weaned mice (3 wk). Subsequently, chambers are inserted in 1 wk old mice. For the experiments with the 1-wk old mice, smaller chambers are prepared from discs (5 mm, I.D.) cut from plastic tips for micropipettes.

Assays

Blood is obtained from the retro-orbital plexus at 1 wk, 1 month, 3 month, 5 month, 10 month and 20 month after implantation of the chambers. The plasma is assayed for hGH, Ob protein and factor IX as described above.

Example 6

Figure 2:
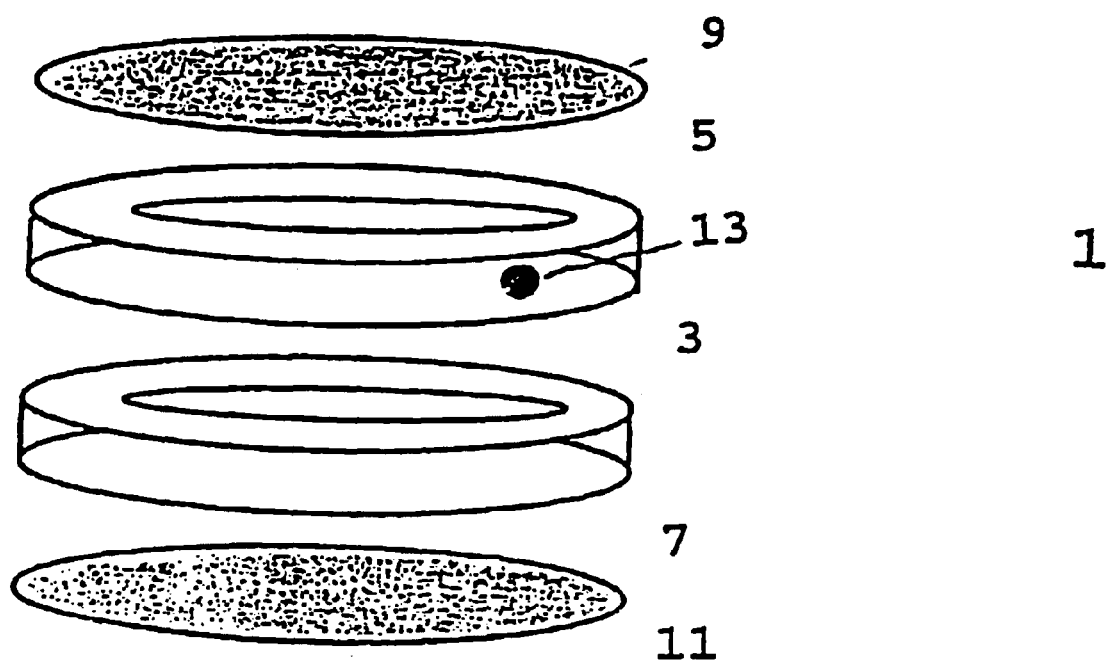
FIG. 2 is a schematic illustration of a diffusion chamber.

Referring to FIG. 2, the diffusion chamber (1) may have a chamber barrel (3) having two ends, a first end (5) and a second end (7). The barrel may be comprised of one or more rings secured together by non-toxic means. The chamber is fitted at each end with a filter, a first filter (9) and a second filter (11). The filters are porous to factors such that the factors may pass between the chamber and the mammal. The filter pores size may be about 0.25 µm or smaller, preferably about 0.1 µm. The filters may be made of plastic, teflon, polyester, or any inert material which is strong, flexible and able to withstand chemical treatments. The filters may be secured in position with rubber gaskets which may also provide a tighter seal. Optionally, the barrel portion of the chamber may have an opening (13) which may be covered by a cap (not shown). The cap may be screw on type of self sealing rubber and fitted to the opening. Inserting cells into the chamber contents may thus be performed by accessing the opening by removing the cap and inserting cells using an ordinary needle and syringe. The chamber may be made of any substance, such as and not limited to plastic, teflon, lucite, titanium, or any inert material, which is non-toxic to, and well tolerated by, mammals. In addition, the chambers should be able to survive sterilization.

The chamber may be implanted in the following non-limiting ways: subcutaneously or intraperitoneally, for example. The chamber may be removed about 24 to about 30 hours after implantation. Alternatively, a refillable chamber may be employed such that the chamber may be re-used for treatments and emptied following treatments.

TABLE I

Conditions for Growth of Primary and Secondary Cultures of MSCs.

| MSCs | Culture conditions | Cells per well ×10$^5$ | APase[a] (mmol min/mg) | TRAP[a] (mmol min/mg) |
|---|---|---|---|---|
| Primary | Standard[a] | 2.0 | 426 | 144 |
|  | Co-cultured[b] | 6.41 | 22.3 | 102 |
|  | Co-cultured[c] (Matrigel) | 6.94 | 42.0 | 105 |
| Secondary[d] | Standard | 1.33 | 2,052 | 75 |
|  | Co-cultured | 7.40 | 362 | 60.6 |
|  | Co-cultured (Matrigel) | 5.08 | 506 | 59.2 |

[a] Whole marrow cells (20 × 10$^6$) from 6-week old mice were cultured in individual 9.5 cm$^2$ wells in 2 ml of 10% FCS and α-MEM. Non-adherent cells were removed on day 3 and the incubation continued in fresh medium until day 7. APase and TRAP was assayed as described in reference 55.
[b] Co-cultured with pieces of bone (one-half femur and one-half tibia) in cell culture inserts (23 mm; 3 μm pore size; Becton Dickinson).
[c] Same as [b], with inserts coated with Matrigel.
[d] Primary cultures on day 10 were detached with 0.25% trypsin and 1 mM EDTA for 5 min at 37° C. followed by gentle scraping. Cells from one well (2 × 10$^5$) were diluted 1:4 and cultured in 9.5 cm$^2$ wells for 7 days with changes of medium on day 3 and day 6.
[e] APase (20, 54) and TRAP (35) Activities were per mg total protein.

TABLE II

Experiments with (a) Transgenic Mice as Recipients; (b) Normal MSCs as Donor Cells; and (c) Decreasing X-Ray Dose.

| Recipient mice | X-ray (cG) | Donor Cells[a] MSCs | Donor Cells[a] Whole marrow | Decrease Bone replacement at 1 month (%) | Decrease in mutated proα1 (1) chains |
|---|---|---|---|---|---|
| Transgenic (3 wk) | 700 | 0.7 × 10$^6$ (N)[a] | 15 × 10$^6$ (TG)[ab] | 10 to 45% (n = 3) | 26 to 73% (n = 3) |
| Transgenic (3 wk) | 350 | 1.2 × 10$^6$ (N) | 2 × 10$^6$ (TG) | 28 to 60% (n = 4) |  |
| Transgenic (3 wk) | 175 | 1.2 × 10$^6$ (N) | 2 × 10$^6$ (TG) | 0 to 40% (n = 4) |  |

[a] (N), normal; (TG), transgenic.
[b] MSCs removed from whole marrow cells before infusion by incubation on plastic culture dish for 4 h at 37° C.

TABLE III

Experiments with (a) Transgenic Mice as Recipients; (b) 10-Fold Increase in Whole Marrow Cells as Donor Cells; and (c) Decreasing X-Ray Dose.

| Recipient mice | X-ray (cG) | Donor Cells[a] MSCs | Donor Cells[a] Whole marrow | Bone replacement at 1 month (%) | Decrease in mutated proα1 (1) chains |
|---|---|---|---|---|---|
| Transgenic (3 wk) | 700 |  | 5 × 10$^6$ (N)[a] | 20 to 38% (n = 3) |  |
| Transgenic (3 wk) | 350 |  | 16 × 10$^6$ (N) (n = 3) | 50 to 78% (n = 3) | 21 to 24% (n = 2) |
| Transgenic (3 wk) | 350 |  | 5 × 10$^6$ (N) | 22 to 45% (n = 4) |  |

[a] (N) whole marrow from normal mice without any treatment to remove MSCs.

TABLE IV

Complex Genetic or Acquired Diseases Treatable by Encapsulated Stromal Cells (Partial List).

| Disease | Deficient or excessive metabolite or protein | Gene defect | Potential therapeutic gene in stromal cells |
|---|---|---|---|
| Growth hormone deficiencies plus growth defects | Low growth hormone in some | Growth hormone in some | Growth hormone |
| Obesity | Unknown | Unknown | Gene for the Ob protein (decreases appetite) |
| Renal disease | Anemia plus other changes | Multiple genes and acquired forms | Erythroprotein |
| Diabetes | Decreased insulin | Multiple | Several genes for insulin synthesis and regulated release (complex) |
| Atherosclerosis | Relatively low HDL levels | Multiple | Gene for Apo-Al (increases HDL in transgenic mice) |
| Osteoporosis | Unknown | Multiple | Estrogen agonist specific for bone cells |
| Infectious diseases, including AIDS | | | Antibodies to infectious agent |
| Autoimmune diseases | | | Antagonists for the immune epitope |

TABLE V

Defined Monogenic Diseases Treatable by Encapsulated Stromal Cells (Partial List).

| Disease | Deficient or excessive metabolite or protein | Gene defect | Potential therapeutic gene in stromal cells |
|---|---|---|---|
| Urea cycle defects | Glutamine | Several different | Glutaminase |
| Branched chain organic acidurias | Keto acids of leucine, isoleucine, and valine | Three different | Specific decarboxylases |
| Adenine deaminase deficiency immuno-deficiency | Deoxy-adenosine | Adenine deaminase | Adenine deaminase |
| Familial lipoprotein | Chylomicrons | Lipoprotein lipase | Lipoprotein lipase |
| Gaucher Disease (type I) | Glucosylceramide | Acid β-glucosidase | Acid β-glucosidase |
| α1-Antitrypsin Deficiency | Low serum protein | α-Antitrypsin | α-Antitrypsin |
| Galactosemia | Increased galactose | One of four enzymes | One of four enzymes |
| Hemophilia | Decreased factor VIII or IX | Factor VIII or IX | Factor VIII or IX |

What is claimed is:

1. An implantable container containing an isolated bone marrow stromal cell which comprises a first expressible gene construct encoding a protein, and a second expressible gene construct encoding a cytotoxic protein, which cytotoxic protein induces selective cell death in the presence of a drug specific for said cytotoxic protein, wherein said first and second expressible gene is under the control of a different promoter, further wherein the container physically isolates the stromal cell from immune cells of an animal when the container is implanted in the animal, and wherein the container has pores for permitting diffusion between the interior and the exterior of the container.

2. The container of claim 1, wherein the first gene construct encodes a secreted protein.

3. The container of claim 1, wherein the container is a microencapsulate stromal cell.

4. The container of claim 1, wherein the container is a biocompatible matrix having the stromal cells incorporated therein.

5. The container of claim 1, wherein the container comprises a membrane having pores which have a diameter not greater than about 0.3 micrometers.

6. The container of claim 5, wherein the container comprises a membrane having pores which have a diameter not greater than about 0.25 micrometers.

7. The container of claim 5, wherein the container comprises a membrane having pores which have a diameter not greater than about 0.1 micrometers.

8. The container of claim 1, wherein the stromal cell comprises a third expressible gene construct encoding a protein.

9. The container of claim 8, wherein the third expressible gene construct encodes an antibiotic resistance protein.

10. The container of claim 8, wherein the first expressible gene construct and the third expressible gene construct are the same gene construct.

11. The container of claim 1, wherein the stromal cell is a human stromal cell.

12. The container of claim 1, wherein the stromal cell is obtained from bone marrow.

13. The container of claim 1, containing at least $10^4$ of the stromal cells.

14. The container of claim 1, containing from $10^4$ to $10^{11}$ of the stromal cells.

15. A method of providing a protein to an animal, the method comprising implanting within the animal a container containing an isolated marrow stromal cell which comprises a first expressible gene construct encoding a protein, and a second expressible gene construct encoding a cytotoxic protein, which cytotoxic protein induces selective cell death in the presence of a drug specific for said cytotoxic protein, wherein said first and second expressible gene is under the control of a different promoter, further wherein the container physically isolates the stromal cell from immune cells of the animal, and wherein the container has pores for permitting diffusion between the interior and the exterior of the container.

16. The method of claim 15, wherein said protein is a secreted protein.

* * * * *